(12) United States Patent
DeFrees

(10) Patent No.: US 8,247,381 B2
(45) Date of Patent: Aug. 21, 2012

(54) BRANCHED WATER-SOLUBLE POLYMERS AND THEIR CONJUGATES

(75) Inventor: Shawn DeFrees, North Wales, PA (US)

(73) Assignee: BioGeneriX AG, Ulm (DE)

( * ) Notice: Subject to any disclaimer, the term of this patent is extended or adjusted under 35 U.S.C. 154(b) by 2 days.

(21) Appl. No.: 12/858,247

(22) Filed: Aug. 17, 2010

(65) Prior Publication Data

US 2010/0331489 A1    Dec. 30, 2010

Related U.S. Application Data

(62) Division of application No. 10/549,445, filed as application No. PCT/US2004/007931 on Mar. 15, 2004, now Pat. No. 7,803,777.

(60) Provisional application No. 60/454,993, filed on Mar. 14, 2003, provisional application No. 60/474,094, filed on May 29, 2003, provisional application No. 60/509,752, filed on Oct. 7, 2003.

(51) Int. Cl.
*A01N 43/04* (2006.01)
*A61K 31/70* (2006.01)

(52) U.S. Cl. ............... 514/23; 514/42; 514/43; 536/4.1; 536/18.7; 536/55.2

(58) Field of Classification Search ........................ None
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,496,689 A | 1/1985 | Mitra |
| 4,565,653 A | 1/1986 | Ives et al. |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,925,796 A | 5/1990 | Bergh et al. |
| 5,032,519 A | 7/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,169,933 A | 12/1992 | Anderson et al. |
| 5,182,107 A | 1/1993 | Friden |
| 5,194,376 A | 3/1993 | Kang |
| 5,202,413 A | 4/1993 | Spinu |
| 5,219,564 A | 6/1993 | Zalipsky et al. |
| 5,281,698 A | 1/1994 | Nitecki |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot et al. |
| 5,369,017 A | 11/1994 | Wong et al. |
| 5,374,541 A | 12/1994 | Wong et al. |
| 5,374,655 A | 12/1994 | Kashem et al. |
| 5,399,345 A | 3/1995 | Schumacher et al. |
| 5,405,753 A | 4/1995 | Brossmer et al. |
| 5,410,016 A | 4/1995 | Hubbell et al. |
| 5,432,059 A | 7/1995 | Bean et al. |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,583,042 A | 12/1996 | Roth |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |

(Continued)

FOREIGN PATENT DOCUMENTS

CA            2500389 A1     4/2004

(Continued)

OTHER PUBLICATIONS

Adelhorst et al., *J. Biol. Chem.*, 269(9): 6275-6278 (1994).
Amersham Pharmacia Biotech, "Hydrophobic Interaction Chromatography: Principles and Methods," 104 pp. (2000).
Brockhausen et al., *Glycoconj. J.*, 15: 595-603 (1998).
Broun et al., *Science*, 282(5392): 1315-1317 (1998).
Costa et al., *J. Biol. Chem.*, 272(17): 11613-11621 (1997).
Culajay et al., *Biochem.*, 39: 7153-7158 (2000).
De Vries et al, *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Edge et.al., *Anal. Biochem.*, 118(1): 131-137 (1981).
Elhalabi et al., *Curr. Med. Chem.*, 6(2): 93-116 (1999).
Espuelas et al., *Bioorg. Med. Chem. Lett.*, 13(15): 2557-2560 (2003).
Fairhall et al., Endocrinology, 131(4): 1963-1969 (1992).

(Continued)

*Primary Examiner* — Patrick Lewis
(74) *Attorney, Agent, or Firm* — Leydig, Voit & Mayer, Ltd.

(57) ABSTRACT

The present invention provides branched water-soluble polymers that allow two or more water-soluble polymers to be conjugated to another species. The branched polymers provide access to therapeutic agents that are conjugated at a single site to two or more water-soluble polymers. The branched polymers are based upon branch points that are simple branched alkyl structures, reactive side-chain amino acids and small peptides of reactive side-chain amino acids, and saccharides. Also provided is a method for preparing mono-disperse poly(ethylene glycol) of a well-defined and determinable molecular weight, and a method for the rational end-functionalization of poly(ethylene glycol). Conjugates of the branched water-soluble polymers with diverse species, e.g., peptides, lipids, glycolipids and small molecules are also provided.

19 Claims, No Drawings

U.S. PATENT DOCUMENTS

| | | |
|---|---|---|
| 5,705,367 A | 1/1998 | Gotschlich |
| 5,716,812 A | 2/1998 | Withers et al. |
| 5,723,121 A | 3/1998 | Takenaga et al. |
| 5,728,554 A | 3/1998 | Bayer et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,874,075 A | 2/1999 | Collins et al. |
| 5,876,980 A | 3/1999 | DeFrees et al. |
| 5,922,577 A | 7/1999 | DeFrees et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden et al. |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,342,382 B1 | 1/2002 | Gotschlich |
| 6,348,558 B1 | 2/2002 | Harris et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,465,220 B1 | 10/2002 | Hassan et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,063,015 B2 | 11/2011 | DeFrees et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0150981 A1 | 10/2002 | Canfield |
| 2002/0168323 A1 | 11/2002 | Gonda |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | DeFrees et al. |
| 2005/0100982 A1 | 5/2005 | DeFrees et al. |
| 2005/0106658 A1 | 5/2005 | DeFrees et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0030521 A1 | 2/2006 | DeFrees et al. |
| 2006/0035224 A1 | 2/2006 | Johansen |
| 2006/0111279 A1 | 5/2006 | DeFrees et al. |
| 2006/0177892 A1 | 8/2006 | DeFrees |
| 2006/0182714 A1 | 8/2006 | Behrens et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |

| | | | | | | |
|---|---|---|---|---|---|---|
| 2007/0254836 A1 | 11/2007 | DeFrees et al. | EP | 0474313 A2 | 3/1992 | |
| 2008/0015142 A1 | 1/2008 | DeFrees et al. | EP | 0585109 A2 | 3/1994 | |
| 2008/0050772 A1 | 2/2008 | DeFrees et al. | EP | 0605963 A2 | 7/1994 | |
| 2008/0070275 A1 | 3/2008 | DeFrees et al. | EP | 1270642 A1 | 1/2003 | |
| 2008/0102083 A1 | 5/2008 | DeFrees et al. | EP | 1428878 A1 | 6/2004 | |
| 2008/0108557 A1 | 5/2008 | Behrens et al. | JP | H03-503759 A | 8/1991 | |
| 2008/0146494 A1 | 6/2008 | DeFrees et al. | JP | H10-307356 A | 11/1998 | |
| 2008/0146782 A1 | 6/2008 | DeFrees et al. | JP | 2001-519784 A | 10/2001 | |
| 2008/0176790 A1 | 7/2008 | DeFrees | WO | WO 87/00056 A1 | 1/1987 | |
| 2008/0187955 A1 | 8/2008 | DeFrees et al. | WO | WO 87/05330 A1 | 9/1987 | |
| 2008/0200651 A1 | 8/2008 | Ostergaard et al. | WO | WO 89/06546 A1 | 7/1989 | |
| 2008/0206808 A1 | 8/2008 | DeFrees et al. | WO | WO 89/10134 A1 | 11/1989 | |
| 2008/0206810 A1 | 8/2008 | Johnson et al. | WO | WO 90/07572 A1 | 7/1990 | |
| 2008/0207487 A1 | 8/2008 | DeFrees et al. | WO | WO 90/08164 A1 | 7/1990 | |
| 2008/0242607 A1 | 10/2008 | DeFrees | WO | WO 90/08823 A1 | 8/1990 | |
| 2008/0242846 A1 | 10/2008 | DeFrees et al. | WO | WO 90/13540 A1 | 11/1990 | |
| 2008/0248959 A1 | 10/2008 | DeFrees | WO | WO 91/14697 A1 | 10/1991 | |
| 2008/0253992 A1 | 10/2008 | DeFrees et al. | WO | WO 92/01055 A1 | 1/1992 | |
| 2008/0255026 A1 | 10/2008 | DeFrees et al. | WO | WO 92/18135 A1 | 10/1992 | |
| 2008/0255040 A1 | 10/2008 | DeFrees | WO | WO 92/22310 A1 | 12/1992 | |
| 2008/0274958 A1 | 11/2008 | DeFrees | WO | WO 93/15189 A1 | 8/1993 | |
| 2008/0280818 A1 | 11/2008 | DeFrees | WO | WO 94/04193 A1 | 3/1994 | |
| 2008/0300173 A1 | 12/2008 | DeFrees | WO | WO 94/05332 A2 | 3/1994 | |
| 2008/0300175 A1 | 12/2008 | DeFrees et al. | WO | WO 94/09027 A1 | 4/1994 | |
| 2008/0305518 A1 | 12/2008 | Klausen et al. | WO | WO 94/15625 A1 | 7/1994 | |
| 2008/0305991 A1 | 12/2008 | DeFrees et al. | WO | WO 94/17039 A1 | 8/1994 | |
| 2008/0305992 A1 | 12/2008 | DeFrees et al. | WO | WO 94/18247 A1 | 8/1994 | |
| 2008/0318850 A1 | 12/2008 | DeFrees et al. | WO | WO 94/28024 A1 | 12/1994 | |
| 2008/0319183 A1 | 12/2008 | DeFrees et al. | WO | WO 95/02421 A1 | 1/1995 | |
| 2009/0028822 A1 | 1/2009 | DeFrees et al. | WO | WO 95/04278 A1 | 2/1995 | |
| 2009/0048440 A1 | 2/2009 | Felo et al. | WO | WO 96/11953 A1 | 4/1996 | |
| 2009/0053167 A1 | 2/2009 | DeFrees | WO | WO 96/21468 A1 | 7/1996 | |
| 2009/0054623 A1 | 2/2009 | DeFrees | WO | WO 96/21469 A1 | 7/1996 | |
| 2009/0055942 A1 | 2/2009 | Ostergaard et al. | WO | WO 96/32491 A1 | 10/1996 | |
| 2009/0081188 A1 | 3/2009 | DeFrees et al. | WO | WO 96/36357 A1 | 11/1996 | |
| 2009/0093399 A1 | 4/2009 | DeFrees et al. | WO | WO 96/40731 A1 | 12/1996 | |
| 2009/0124544 A1 | 5/2009 | DeFrees | WO | WO 96/40881 A1 | 12/1996 | |
| 2009/0137763 A1 | 5/2009 | DeFrees et al. | WO | WO 97/05330 A1 | 2/1997 | |
| 2009/0143292 A1 | 6/2009 | Hinderer et al. | WO | WO 98/05363 A2 | 2/1998 | |
| 2009/0169509 A1 | 7/2009 | DeFrees et al. | WO | WO 98/31826 A1 | 7/1998 | |
| 2009/0176967 A1 | 7/2009 | Stennicke | WO | WO 98/41562 A1 | 9/1998 | |
| 2009/0203579 A1 | 8/2009 | DeFrees et al. | WO | WO 98/51784 A1 | 11/1998 | |
| 2009/0227504 A1 | 9/2009 | Klausen et al. | WO | WO 98/58964 A1 | 12/1998 | |
| 2009/0240028 A1 | 9/2009 | Behrens et al. | WO | WO 99/00150 A1 | 1/1999 | |
| 2009/0247450 A1 | 10/2009 | Mack | WO | WO 99/14259 A1 | 3/1999 | |
| 2009/0252720 A1 | 10/2009 | Ostergaard et al. | WO | WO 99/22764 A1 | 5/1999 | |
| 2009/0253166 A1 | 10/2009 | Zundel et al. | WO | WO 99/34833 A1 | 7/1999 | |
| 2009/0264366 A1 | 10/2009 | Johansen et al. | WO | WO 99/45964 A1 | 9/1999 | |
| 2009/0292110 A1 | 11/2009 | DeFrees | WO | WO 99/48515 A1 | 9/1999 | |
| 2009/0305967 A1 | 12/2009 | DeFrees et al. | WO | WO 99/55376 A1 | 11/1999 | |
| 2010/0009902 A1 | 1/2010 | DeFrees | WO | WO 00/23114 A2 | 4/2000 | |
| 2010/0015684 A1 | 1/2010 | DeFrees et al. | WO | WO 00/26354 A1 | 5/2000 | |
| 2010/0028939 A1 | 2/2010 | Behrens et al. | WO | WO 00/65087 A1 | 11/2000 | |
| 2010/0029555 A1 | 2/2010 | Tonon et al. | WO | WO 01/02017 A2 | 1/2001 | |
| 2010/0035299 A1 | 2/2010 | DeFrees et al. | WO | WO 01/05434 A2 | 1/2001 | |
| 2010/0041872 A1 | 2/2010 | DeFrees et al. | WO | WO 01/39788 A2 | 6/2001 | |
| 2010/0048456 A1 | 2/2010 | DeFrees et al. | WO | WO 01/49830 A2 | 7/2001 | |
| 2010/0056428 A1 | 3/2010 | Behrens | WO | WO 01/51510 A2 | 7/2001 | |
| 2010/0075375 A1 | 3/2010 | DeFrees et al. | WO | WO 01/58493 A1 | 8/2001 | |
| 2010/0081791 A1 | 4/2010 | DeFrees et al. | WO | WO 01/58935 A2 | 8/2001 | |
| 2010/0113743 A1 | 5/2010 | DeFrees et al. | WO | WO 01/60411 A1 | 8/2001 | |
| 2010/0120666 A1 | 5/2010 | Zopf et al. | WO | WO 01/76640 A2 | 10/2001 | |
| 2010/0174059 A1 | 7/2010 | DeFrees et al. | WO | WO 01/88117 A2 | 11/2001 | |
| 2010/0210507 A9 | 8/2010 | DeFrees et al. | WO | WO 02/02597 A2 | 1/2002 | |
| 2010/0286067 A1 | 11/2010 | DeFrees | WO | WO 02/02764 A2 | 1/2002 | |
| 2010/0322940 A1 | 12/2010 | Bayer | WO | WO 02/13843 A2 | 2/2002 | |
| 2010/0330645 A1 | 12/2010 | DeFrees et al. | WO | WO 02/13873 A2 | 2/2002 | |
| 2010/0331489 A1 | 12/2010 | DeFrees | WO | WO 02/44196 A1 | 6/2002 | |
| 2011/0003744 A1 | 1/2011 | DeFrees et al. | WO | WO 02/053580 A2 | 7/2002 | |
| 2011/0177029 A1 | 7/2011 | Defrees | WO | WO 02/074806 A2 | 9/2002 | |
| 2011/0223646 A1 | 9/2011 | Schwartz et al. | WO | WO 02/092619 A2 | 11/2002 | |
| 2011/0318780 A1 | 12/2011 | DeFrees | WO | WO 03/017949 A2 | 3/2003 | |
| 2012/0016105 A1 | 1/2012 | DeFrees et al. | WO | WO 03/031464 A2 | 4/2003 | |
| | | | WO | WO 03/045980 A2 | 6/2003 | |
| FOREIGN PATENT DOCUMENTS | | | WO | WO 03/046150 A2 | 6/2003 | |
| CA | 2511814 A1 | 7/2004 | WO | WO 03/093448 A2 | 11/2003 | |
| DE | 19852729 A1 | 5/2000 | WO | WO 04/000366 A1 | 12/2003 | |
| EP | 0370205 A2 | 5/1990 | WO | WO 2004/009838 A2 | 1/2004 | |
| EP | 0459630 A2 | 12/1991 | WO | WO 2004/010327 A2 | 1/2004 | |

| | | |
|---|---|---|
| WO | WO 2004/022004 A2 | 3/2004 |
| WO | WO 2004/033651 A2 | 4/2004 |
| WO | WO 2004/046222 A1 | 6/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/096148 A2 | 11/2004 |
| WO | WO 2004/099231 A2 | 11/2004 |
| WO | WO 2004/103275 A2 | 12/2004 |
| WO | WO 2005/012484 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/091944 A2 | 10/2005 |
| WO | WO 2005/121331 A2 | 12/2005 |
| WO | WO 2006/010143 A2 | 1/2006 |
| WO | WO 2006/014349 A2 | 2/2006 |
| WO | WO 2006/014466 A2 | 2/2006 |
| WO | WO 2006/020372 A2 | 2/2006 |
| WO | WO 2006/031811 A2 | 3/2006 |
| WO | WO 2006/050247 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/105426 A2 | 10/2006 |
| WO | WO 2006/121569 A2 | 11/2006 |
| WO | WO 2006/127910 A2 | 11/2006 |
| WO | WO 2007/022512 A2 | 2/2007 |
| WO | WO 2007/056191 A2 | 5/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Feldman et al., *Proc. Natl. Acad. Sci. USA*, 1028): 3016-3021 (2005).
Francis et al., *Intl. J. Hematol.*, 68(1): 1-18 (1998).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Hansen et al., *Biochem J.*, 308: 801-813 (1995).
Haro et al., *Biochem. Biophys. Res. Comm.*, 228(2): 549-556 (1996).
Herscovics et al., *FASEB J.*, 7(6): 540-550 (1993).
Höglund, *Med. Oncol.*, 15(4): 229-233 (1998).
Hu et al., *Mol. Cell. Biol.*, 18(10): 6063-6074 (1998).
Jezek et al., *J. Peptide Sci.*, 5: 46-55 (1999).
Kaneko et al., *Cytogenet. Cell Genet.*, 86(3-4): 329-330 (1999).
Kaneko et al., *FEBS Lett.*, 452(3): 237-242 (1999).
Keene et al., *J. Biol. Chem.*, 264(9): 4769-4775 (1989).
Kimura et al., *Proc. Natl. Acad. Sci. USA*, 96(8): 4530-4535 (1999).
Kisselev, *Structure*, 10(1): 8-9 (2002).
Kornfeld et al., *Ann. Rev. Biochem.*, 54: 631-664 (1985).
Kukowska-Latallo et al., *Genes Dev.*, 4(8): 1288-1303 (1990).
Kukuruzinska et al., *Proc. Natl. Acad. Sci. USA*, 84(8): 2145-2149 (1987).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lönnberg, *Curr. Org. Synth.*, 6(4): 400-425 (2009).
Malissard et al., *Biochem. Biophys. Res. Commun.*, 267(1): 169-173 (2000).
Mollicone et al., *Eur. J. Biochem.*, 191(1): 169-176 (1990).
Monaco et al., *Gene*, 180: 145-150 (1996).
Nagata et al., *EMBO J.*, 5(3): 575-581 (1986).
Natsuka et al., *J. Biol. Chem.*, 269(24): 16789-16794 (1994).
Nunez et al., *Can. J. Chem.*, 59(14): 2086-2095 (1981).

Oh-Eda et al., *J. Biol. Chem.*, 265: 11432-11435 (1990).
Orlean, "vol. III: The Molecular and Cellular Biology of the Yeast Saccharomyces: Cell Cycle and Cell Biology", in *Biogenesis of Yeast Wall and Surface Components*, Chapter 3, pp. 229-362, Cold Spring Harbor Laboratory Press (1997).
Orskov et al., *J. Biol. Chem.*, 264(22): 12826-12829 (1989).
Palcic et al., *Carbohydr. Res.*, 190(1): 1-11 (1989).
Prati et al., *Biotech and Bioeng.*, 79(5): 580-585 (2002).
Prieels et al., *J. Biol. Chem.*, 256(20): 10456-10463 (1981).
R & D Systems, Fibroblast Growth Factors (FGFs), Internet page from www.rndsystems.com/mini_review_detail_objectname_MR01_FGFs.aspx, 2001, printed Mar. 10, 2011.
Rasko et al., *J. Biol. Chem.*, 275(7): 4988-4994 (2000).
Saxon et al., *J. Am. Chem. Soc.*, 124(50): 14893-14902 (2002).
Seffernick et al., *J. Bacteriol.*, 183(8): 2405-2410 (2001).
Sinclair et al., *J. Pharm. Sci.*, 94: 1626-1635 (2005).
Sojar et al., *Arch. Biochem. Biophys.*, 259(1): 52-57 (1987).
Staudacher, *Trends Glycosci. Glycotechnol.*, 8(44): 391-408 (1996).
Stemmer, *Nature*, 370(6488): 389-391 (1994).
Stemmer, *Proc. Natl. Acad. Sci. USA*, 91(22): 10747-10751 (1994).
Trottein et al., *Mol. Biochem. Parasitol.*, 107(2): 279-287 (2000).
Van Tetering et al., *FEBS Lett.*, 461(3): 311-314 (1999).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(6): 4152-4160 (1992).
Weston et al., *J. Biol. Chem.*, 267(34): 24575-24584 (1992).
Wishart et al., *J. Biol. Chem.*, 270(45): 26782-26785 (1995).
Witkowski et al., *Biochemistry*, 38(36): 11643-11650 (1999).
Zhang et al., *Biochim. Biophys. Acta*, 1425: 441-452 (1998).
Abeijon et al., *J. Biol. Chem.*, 261(24): 11374-11377 (1986).
Abuchowski et al., *J. Biol. Chem.*, 252(11): 3578-3581 (1977).
Abuchowski et al., *J. Biol. Chem.*, 252(11): 3582-3586 (1977).
Abuchowski et al., *Cancer Biochem. Biophys.*, 7(2): 175-186 (1984).
Ailor et al., *Glycobiology*, 10(8): 837-847 (2000).
Alam et al., *J. Biotechnol.*, 65(2-3): 183-190 (1998).
Allegre et al., *J. Memb. Sci.*, 269(1-2): 109-117 (2006).
Altmann et al., *Glycoconj. J.*, 16(2): 109-123 (1999).
Aplin et al., *CRC Crit. Rev. Biochem.*, 10(4): 259-306 (1981).
Barrios et al., *J. Mol. Recognit.*, 17(4):332-338 (2004).
Beauchamp et al., *Anal. Biochem.*, 131(1): 25-33 (1983).
Bedard et al., *Cytotechnology*, 15(1-3):129-138 (1994).
Bennett et al., *J. Biol. Chem.*, 273(46): 30472-30481 (1998).
Bennett et al., *FEBS Lett.*, 460(2): 226-230 (1999).
Berger etas., *Blood*, 71(6): 1641-1647 (1988).
Berg-Fussman et al., *J. Biol. Chem.*, 268(20): 14861-14866 (1993).
Bhadra et al., *Pharmazie*, 57(1): 5-29 (2002).
Bhatia et al., *Anal. Biochem.*, 178(2): 408-413 (1989).
Bickel et al., *Adv. Drug Deliv. Rev.*, 46(1-3): 247-279 (2001).
Bijsterbosch et al., *Eur. J. Biochem.*, 237(2): 344-349 (1996).
Bjoern et al., *J. Biol. Chem.*, 266(17): 11051-11057 (1991).
Boccu et al., *Z. Naturforsch.*, 38c: 94-99 (1983).
Boime et al., *Recent Prog. Norm. Res.*, 54: 271-289 (1999).
Boissel et al., *J. Biol. Chem.*, 268(21): 15983-15993 (1993).
Bork et al., *Trends Genet.*, 12(10): 425-427 (1996).
Bork, *Genome Res.*, 10(4): 398-400 (2000).
Bouizar et al., *Eur. J. Biochem.*, 155(1): 141-147 (1986).
Boyd et al., *Mol. Immunol.*, 32(17-18): 1311-1318 (1995).
Brenner, *Trends Genet.*, 15(4): 132-133 (1999).
Brockhausen et al., *Acta Anatomica*, 161: 36-78 (1998).
Browning et al., *J. Immunol.*, 143(6): 1859-1867 (1989).
Bückmann et al., *Makromol. Chem.*, 182(5): 1379-1384 (1981).
Burns et al., *Blood*, 99(12): 4400-4405 (2002).
Butnev et al., *Biol. Reprod.*, 58(2): 458-469 (1998).
Byun et al., *ASAIO J.*, 38(3): M649-M653 (1992).
Cantin et al., *Am. J. Respir. Cell Mol. Biol.*, 27(6): 659-665 (2002).
Casares et al., *Nat. Biotechnol.*, 19(2): 142-147 (2001).
Chaffee et al., *J. Clin. Invest.*, 89(5): 1643-1651 (1992).
Charter et al., *Glycobiology*, 10(10): 1049-1056 (2000).
Chern et al., *Eur. J. Biochem.*, 202(2): 225-229 (1991).
Chiba et al., *Biochem. J.*, 308(2): 405-409 (1995).
Chrisey et al., *Nucleic Acids Res.*, 24(15): 3031-3039 (1996).
Clark et al., *J. Biol. Chem.*, 271(36): 21969-21977 (1996).
Cohn et al., *J. Biomed. Mater. Res,.* 22(11): 993-1009 (1988).

Cointe et al., *Glycobiology*, 10(5): 511-519 (2000).
Conradt et al., *J. Biol. Chem.*, 262(30): 14600-14605 (1987).
Cope et al., *Mol. Microbiol.*, 5(5): 1113-1124 (1991).
Copeland, "Enzymes: A Practical Introduction to Structure, Mechanism and Data Analysis" 2nd ed., Wiley-VCH, New York, pp. 146-150 (2000).
Crout et al., *Curr. Opin. Chem. Biol.*, 2(1): 98-111 (1998).
DeFrees et al., *Glycobiology*, 16(9): 833-843 (2006).
Delgado et al., *Biotechnol. Appl. Biochem.*, 12(2): 119-128 (1990).
Delgado et al., *Crit. Rev. Ther. Drug Carrier Syst.*, 9(3-4): 249-304 (1992).
Doerks et al., *Trends Genet.*, 14(6): 248-250 (1998).
Douglas et al., *J. Am. Chem. Soc.*, 113(13): 5095-5097 (1991).
Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Durieux et al., *Tetrahedron Lett.*, 42(12): 2297-2299 (2001).
Dwek et al., *J. Anat.*, 187(Pt. 2): 279-292 (1995).
Eavarone et al., *J. Biomed. Mater. Res.*, 51(1): 10-14 (2000).
EMBL Accession No. M80599 and M86935, "*Escherichia coli* lipopolysaccharide core biosynthesis protein operon (rfaQ, rfaP, rfaG, rfaB, rfaI, and rfaJ) genes, complete cds," (Jan. 23, 1992).
EMBL Accession No. S56361, "rfa gene cluster: rfaP-lipopolysaccharide core production protein, rfaB=lipopolysaccharide core product protein [Salmonella typhimurium LT2, Genomic, 3 genes, 815 nt," (May 4, 1993).
EMBL Accession No. U0039, "*E. coli* chromosomal region from 76.0 to 81.5 minutes," (Jun. 2, 1994).
Fan et al., *J. Biol. Chem.*, 272(43): 27058-27064 (1997).
Felix et al., *J. Peptide Res.*, 63: 85-90 (2004).
Fibi et al., *Blood*, 85(5): 1229-1236 (1995).
Fischer et al., *Thromb. Res.*, 89(3): 147-150 (1998).
Flynn et al., *Curr. Opin. Oncol.*, 12(6): 574-581 (2000).
Fritz et al., *Proc. Natl. Acad. Sci. USA*, 101(43): 15307-15312 (2004).
Fritz et al., *J. Biol. Chem.*, 281(13): 8613-8619 (2006).
Garnett et al., *Adv. Drug Deliv. Rev.*, 53(2): 171-216 (2002).
Gatot et al., *J. Biol. Chem.*, 273(21): 12870-12880 (1998).
Ge et al., *J. Biol. Chem.*, 272(34): 21357-21363 (1997).
Genbank Accession No. U02304, "Mus musculus LAF1 glycosaminoglycan N-acetylglucosaminyl N-deacetylase/N-sulfotransferase mRNA, complete cds," (Mar. 8, 1994).
Genbank Accession No. D49915, "Gallus gallus mRNA for chondroitin 6-sulfotransferase, complete cds," (Sep. 1, 1995).
Genbank Accession No. U18918, "Human heparin sulfate-N-deacetylase/N-sulfotransferase mRNA, clone HSST, complete cds," (Oct. 1, 1995).
Gervais et al., *Glycobiology*, 13(3): 179-189 (2003).
Gilbert et al., *Cytotechnology*, 22(1-3): 211-216 (1996).
Gillis et al., *Behring Inst. Mitt.*, 83: 1-7 (1988).
Ginns, PEG Glucocerebrosidase, Internet page from www.gaucher.org.uk/peg2.prg, Nov. 1994, printed Jun. 21, 2002.
Gotschlich, *J. Exp. Med.*, 180(6): 2181-2190 (1994).
Grabenhorst et al., *Eur. J. Biochem.*, 215(1): 189-197 (1993).
Grabenhorst et al., *J. Biol. Chem.*, 274(51): 36107-36116 (1999).
Grodberg et al., *Eur. J. Biochem.*, 218(2): 597-601 (1993).
Gross et al., *Biochemistry*, 28(18): 7386-7392 (1989).
Gross, *Eur. J. Biochem.*, 203(1-2): 269-275 (1992).
Hagen et al., *J. Biol. Chem.*, 274(10): 6797-6803 (1999).
Hagen et al., *J. Biol. Chem.*, 276(20): 17395-17404 (2001).
Hall, *Methods Mol. Biol.*, 166: 139-154 (2001).
Haneda et al., *Carbohydr. Res.*, 292: 61-70 (1996).
Hang et al., *J. Am. Chem. Soc.*, 123(6): 1242-1243 (2001).
Harris et al., *Nat. Rev. Drug Discov.*, 2(3): 214-221 (2003).
Harris et al., Abstracts of Papers of the American Chemical Society, V 201, APR, P 64-POLY, pp. 154-155 (1991).
Harris, *J. Macromol. Science, Rev. Macromol. Chem. Phys.*, C25(3): 325-373 (1985).
Harris (ed.), "Poly(Ethylene Glycol) Chemistry: Biotechnical and Biomedical Applications", Plenum Press, New York (1992) (Title Pages only).
Harris et al. (eds.), "Poly(ethylene glycol): Chemistry and Biological Applications," ACS Symposium Series, vol. 680, American Chemical Society (1997) (Title Pages only).

Hassan et al., *J. Biol. Chem.*, 275(49): 38197-38205 (2000).
Hassan et al., *Carbohydrates in Chemistry and Biology*, Part II, 3: 273-292 (2000).
Hayes et al., *J. Biol. Chem.*, 268(22): 16170-16178 (1993).
Hellstrom et al., *Methods Mol. Biol.*, 166: 3-16 (2001).
Hermanson et al., *Immobilized Affinity Ligand Techniques*, Academic Press (1992) (Table of Contents).
Hermanson, *Bioconjugate Techniques*, Academic Press, San Diego (1996) (Table of Contents).
Hermentin, et al., *Glycobiology*, 6(2): 217-230 (1996).
Hills et al., *Am. Biotechnol. Lab.*, 20(11): 30 (2002).
Hink et al., *Biotechnol. Prog.*, 7(1): 9-14 (1991).
Hollister et al., *Glycobiology*, 11(1): 1-9 (2001).
Hounsell et al., *Glycoconj. J.*, 13(1): 19-26 (1996).
Ichikawa et al., *J. Am. Chem. Soc.*, 114(24): 9283-9298 (1992).
Ikonomou et al., *In Vitro Cell. Dev. Biol. Anim.*, 37(9): 549-559 (2001).
Inlow et al., *J. Tissue Cult. Methods*, 12(1): 13-16 (1989).
Inoue et al., *Biotechnol. Annu. Rev.*, 1: 297-313 (1995).
Ito et al., *Pure Appl. Chem.*, 65(4): 753-762 (1993).
Jackson et al., *Anal. Biochem.*, 165(1): 114-127 (1987).
Jarvis et al., *Curr. Opin. Biotechnol.*, 9(5): 528-533 (1998).
Joppich et al., *Makromol. Chem.*, 180: 1381-1384 (1979).
Joshi et al., *J. Biol. Chem.*, 265(24): 14518-14525 (1990).
Jung et al., *Biochim. Biophys. Acta*, 761(2): 152-162 (1983).
Kajihara et al., *Carbohydrate Research*, 315: 137-141 (1999).
Kalsner et al., *Glycoconj. J.*, 12(3): 360-370 (1995).
Kasina et al., *Bioconjug. Chem.*, 9(1): 108-117 (1998).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keppler et al., *Glycobiology*, 11(2): 11R-18R (2001).
Kitamura et al., *Biochem. Biophys. Res. Commun.*, 171(3): 1387-1394 (1990).
Kitamura et al., *Cancer Res.*, 51(16): 4310-4315 (1991).
Kobayashi et al., *Eur. J. Nucl. Med.*, 27(9):1334-1339 (2000).
Kodama et al., *Tetrahedron Lett.*, 34(40): 6419-6422 (1993).
Koeller et al., *Nat. Biotechnol.*, 18(8): 835-841 (2000).
Koeller et al., *Nature*, 409(6817): 232-240 (2001).
Koide et al., *Biochem. Biophys. Res. Commun.*, 111(2): 659-667 (1983).
Kreitman, *Curr Pharm Biotechnol*, 2(4): 313-325 (2001).
Kuhn et al., *J. Biol. Chem.*, 270(49): 29493-29497 (1995).
Lai et al, *J. Biol. Chem.*, 261(7): 3116-3121 (1986).
Langer, *Science*, 249(4976): 1527-1533 (1990).
Lau et al., *J. Biotechnol.*, 75(2-3): 105-115 (1999).
Lee et al., *Biochemistry*, 28(4): 1856-1861 (1989)
Lee-Huang et al., *Proc. Natl. Acad. Sci. USA*, 81(9): 2708-2712 (1984).
Legault et al., *J. Biol. Chem.*, 270(36): 20987-20996 (1995).
Leung, *J Immunol.* 154(11): 5919-5926 (1995).
Li et al., *Trends Pharmacol. Sci.*, 23(5): 206-209 (2002).
Li et al., *Med. Res. Rev.*, 22(3): 225-250 (2002).
Licari et al., *Biotechnol. Bioeng.*, 39(4): 432-441 (1992).
Licari et al.,*Biotechnol. Bioeng.*, 39(9): 932-944 (1992).
Lin et al., *Proc. Natl. Acad. Sci. USA*, 82: 7580-7584 (1985).
Liu et al., *Chem. Eur. J.*, 2(11): 1359-1362 (1996).
Long et al., *Exp. Hematol.*, 34(6): 697-704 (2006).
Lord et al., *Clin. Cancer Res.*, 7(7): 2085-2090 (2001).
Lougheed et al, *J. Biol. Chem.*, 274(53): 37717-37722 (1999).
Luckow et al., *Curr. Opin. Biotechnol.*, 4(5): 564-572 (1993).
Lund et al., *FASEB J.*, 9(1): 115-119 (1995).
Lund et al., *J. Immunol.*, 157(11): 4963-4969 (1996).
Mahal et al., *Science*, 276(5315): 1125-1128 (1997).
Maranga et al., *Biotechnol. Bioeng.*, 84(2): 245-253 (2003).
Maras et al., *J Biotechnol.*, 77(2-3): 255-263 (2000).
Meynial-Salles et al., *J. Biotechnol.*, 46(1): 1-14 (1996).
Miller, *Curr. Opin. Genet. Dev.*, 3(1): 97-101 (1993).
Min et al., *Endocr. J.*, 43(5): 585-593 (1996).
Mistry et al., *Lancet*, 348(9041): 1555-1559 (1996).
Morimoto et al., *Glycoconj. J.*, 13(6): 1013-1020 (1996).
Muller et al., *J. Biol. Chem.*, 272(40): 24780-24793 (1997).
Muller et al., *J. BioL Chem.*, 274(26): 18165-18172 (1999).

NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Ngo et al., "The Protein Folding Problem and Tertiary Structure Prediction, Chapter 14: Computational Complexity Protein Structure Prediction, and the Levinthal Paradox," pp. 433-440 and 492-495 (1994).
Nilsson et al., *Methods Enzymol.*, 104: 56-69 (1984).
O'Connell et al., *J. Biol. Chem.*, 267(35): 25010-25018 (1992).
Oetke et al., *J. Biol. Chem.*, 277(8): 6688-6695 (2002).
Olson et al., *J. Biol. Chem.*, 274(42): 29889-29896 (1999).
Palacpac et al., *Proc. Natl. Acad. Sci. USA*, 96(8): 4692-4697 (1999).
Park et al., *J. Biol. Chem.*, 261(1): 205-210 (1986).
Paulson et al., *J. Biol. Chem.*, 252(23): 8624-8628 (1977).
Plummer et al., *J. Biol. Chem.*, 270(22): 13192-13196 (1995).
PNGase-F Amidase Sequence from *F. Meningosepticum* (RN 128688-70-0) (2007).
PNGase-F Amidase Sequence from *F. Meningosepticum* (RN 128688-71-1) (2007).
Pyatak et al., *Res. Commun. Chem. Pathol. Pharmacol.*, 29(1): 113-127 (1980).
Rabouille et al., *J Cell Sci.*, 112(Pt. 19): 3319-3330 (1999).
Reff et al., *Cancer Control*, 9(2): 152-166 (2002).
Rosenthal et al., *Methods Enzymol.*, 235: 253-285 (1994).
Rotondaro et al., *Mol. Biotech.*, 11: 117-128 (1999).
Rudikoff et al., *Proc. Natl. Acad. Sci. USA*, 79(6):1979-1983 (1982).
Sadler et al., *Methods Enzymol.*, 83: 458-514 (1982).
Sandberg et al., *Semin. Hematol.*, 38(2 Suppl. 4): 4-12 (2001).
Saneyoshi et al., *Biol. Reprod.*, 65(6): 1686-1690 (2001).
Sasaki et al., *J. Biol. Chem.*, 262(25): 12059-12076 (1987).
Sasaki et al., *J.Biol. Chem.*, 269: 14730-14737 (1994).
Saxon et al., *Science*, 287(5460): 2007-2010 (2000).
Schlaeger, *Cytotechnology*, 20(1-3): 57-70 (1996).
Schwientek et al., *Gene*, 145(2): 299-303 (1994).
Schwientek et al., *J. Biol. Chem.*, 277(25): 22623-22638 (2002).
Scouten, *Methods Enzymol.*, 135: 30-65 (1987).
Seely et al., *J. Chromatog.*, 908: 235-241 (2001).
Seitz, *Chembiochem.*, 1(4): 214-246 (2000).
Shah et al., *J. Pharm. Sci.*, 85(12): 1306-1311 (1996).
Shapiro et al., *Blood*, 105(2): 518-525 (2005).
Shen et al., *Biochem. Biophys. Res. Commun.*, 102(3): 1048-1054 (1981).
Shinkai et al., *Prot. Exp. Purif.*, 10: 379-385 (1997).
Singh et al., *Chem. Commun.*, 1996(8): 993-994 (1996).
Sinha et al., *Infect. Immun.*, 29(3): 914-925 (1980).
Skolnick et al., *Trends Biotechnol.*, 18(1): 34-39 (2000).
Smith et al., *Nat. Biotechnol.*, 15(12): 1222-1223 (1997).
Snider et al., *J. Chromatogr., A* 599(1-2): 141-155 (1992).
Song et al., *J. Pharmacol. Exp. Ther.*, 301(2): 605-610 (2002).
Srinivasachar et al., *Biochemistry*, 28(6): 2501-2509 (1989).
Stephens et al., *Eur. J. Biochem.*, 133(1): 155-162 (1983).
Stephens et al., *Eur. J. Biochem.*, 133(3): 481-489 (1983).
Stephens et al., *Eur. J. Biochem.*, 135(3): 519-527 (1983).
Strausberg et al., *Proc Natl Acad Sci USA*, 99(26): 16899-16903 (2002).
Swiss-PROT Accession No. P19817, Lipopolysaccharide 1, 2-glucosyltransferase (EC 2.4.1.58) (Feb. 1, 1991).
Swiss-PROT Accession No. P25740, Lipopolysaccharide core biosynthesis protein rfaG (Glucosyltransferase I) (May 1, 1992).
Swiss-PROT Accession No. P27129, Lipopolysaccharide 1, 2-glucosyltransferase (Ec 2.4.1.58)•(Aug. 1, 1992).
Takane et al., *J Pharmacol Exp Ther.*, 294(2): 746-752 (2000).
Takeda et al., *Trends Biochem. Sci.*, 20(9): 367-371 (1995).
Takeuchi et al., *J. Biol. Chem.*, 265(21): 12127-12130 (1990).
Taniguchi et al., *Proteomics*, 1(2): 239-247 (2001).
Tanner et al., *Biochim. Biophys. Acta*, 906(1): 81-99. (1987).
Taylor et al., Protein Immobilization Fundamentals and Applications, Manual (1991).
Ten Hagen et al., *J. Biol. Chem.*, 274(39): 27867-27874 (1999).
Tenno et al., *J. Biol. Chem.*, 277(49): 47088-47096 (2002).
Thotakura et al., *Meth. Enzym.*, 138: 350-9 (1987).
Tsuboi et al., *Arch. Biochem. Biophys.*, 374(1): 100-106 (2000).
Tsunoda et al., *J. Pharmacol. Exp. Ther.*, 209(1): 368-372 (1999).
Tuddenham, *Nature*, 419(6902): 23-24 (2002).
Udenfriend et al., *Annu. Rev. Biochem.*, 64: 563-591 (1995).
Ulloa-Aguirre et al., *Endocrine*, 11(3): 205-215 (1999).
Uludag et al., *Biotechnol. Prog.*, 18(3): 604-611 (2002).
Urdal et al, *J. Chromatogr.*, 296: 171-179 (1984).
Van Berkel et al., *Biochem. J.*, 319(Pt. 1): 117-122 (1996).
Van Reis et al., *Biotechnol. Bioeng.*, 38(4): 413-422 (1991).
Veronese et al., *Appl. Biochem. Biotechnol.*, 11(2): 141-152 (1985).
Vitetta et al., *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., *Crit. Rev. Ther. Drug Carrier Syst.*, 18(1): 1-76 (2001).
Wang et al., *Tetrahedron Lett.*, 37(12): 1975-1978 (1996).
Wang et al., *Protein Eng.*, 11(12): 1277-1283 (1998).
Wellhoner et al., *J. Biol. Chem.*, 266(7): 4309-4314 (1991).
Wells, *Biochemistry*, 29(37): 8509-8517 (1990).
White et al., *J. Biol. Chem.*, 270(41): 24156-24165 (1995).
Witte et al., *J. Am. Chem. Soc.*, 119(9): 2114-2118 (1997).
Witte et al., *Cancer and Metastasis Rev.*, 17: 155-161 (1998).
Woghiren et al., *Bioconjug. Chem.*, 4(5): 314-318 (1993).
Wong et al., *J. Org. Chem.*, 47(27): 5416-5418 (1982).
Wong et al., *Enzyme Microb Technol.*, 14(11): 866-874 (1992).
Wong et al., *Biotechnol. Bioeng.*, 49(6): 659-666 (1996).
Woods et al., *Eur. J. Cell Biol.*, 50(1): 132-143 (1989).
Wright et al., *J. Immunol.*, 160(7): 3393-3402 (1998).
Wu et al., *J. Drug Target.*, 10(3): 239-245 (2002).
Xing et al., *Biochem. J.*, 336(Pt. 3): 667-673 (1998).
Yamada et al., *Biochemistry*, 20(17): 4836-4842 (1981).
Yamamoto et al., *Carbohydr. Res.*, 305(3-4): 415-422 (1998).
Yarema et al., *J. Biol. Chem.*, 273(47): 31168-31179 (1998).
Yoshida et al., *Glycobiology*, 9(1): 53-58 (1999).
Yoshitake et al., *Biochemistry*, 24(14): 3736-3750 (1985).
Younes et al., *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, *Bioconjug. Chem.*, 6(2): 150-165 (1995).
Zarling et al., *J. Immunol.*, 124(2): 913-920 (1980).
Zheng et al., *Biotechnol. Bioeng.*, 65(5): 600-604 (1999).
Zhou et al., 1994, *Mol. Microbiol.*, 14(4): 609-618 (1994).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.

Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.

Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Brumeanu et al., *J. Immunol. Meth.*, 183: 185-197 (1995).
Deacon, *Diabetes*, 54: 2181-2189 (2004).
Gross et al., *Eur. J. Biochem,.* 177(3): 583-589 (1988).
Guo et al., *Appl. Biochem. Biotechnol.*, 68(1-2): 1-20 (1997).
Hällgren et al., *J. Carb. Chem.*, 14(4-5): 453-464 (1995).
Kennedy, "Hydrophobic-Interaction Chromatography," in *Current Protocols in Protein Science*, pp. 8.4.1-8.4.21, Wiley (1995).

Krystal et al., *Blood*, 67(1): 71-99 (1986).
O'Shannessy et al., *J. Appl. Biochem.*, 7: 347-355 (1985).
Quelle et al., *Blood*, 74(2): 652-657 (1989).
Rathnam et al., *Biochim. Biophys. Acta*, 624(2): 436-442 (1980).
Schwarz et al., *Nucl. Med. Biol.*, 26(4):383-388 (1999).
Srivastava et al., *J. Biol. Chem.*, 267(31): 22356-22361 (1992).
Tom et al., *AAPS Journal*, 9(2): E227-E234 (2007).
UPTIMA, Detergents: Solubilization of Biomolecules, Internet page from www.interchim.com/interchim/bio/produits_uptima/product_line/p1p_detergents.htm, 2001, printed Nov. 14, 2011.
Veronese, *Biomaterials*, 22(5): 405-417 (2001).
Yin et al., *Pharm. Res.*, 21(12): 2377-2383 (2004).

BRANCHED WATER-SOLUBLE POLYMERS AND THEIR CONJUGATES

CROSS-REFERENCES TO RELATED APPLICATIONS

The present application is a divisional of U.S. patent application Ser. No. 10/549,445, filed Jul. 31, 2006, and issued as U.S. Pat. No. 7,803,777, which is the U.S. National Phase of International Patent Application No. PCT/US2004/007931, filed Mar. 15, 2004, which claims the benefit of U.S. Provisional Patent Application No. 60/454,993, filed Mar. 14, 2003, U.S. Provisional Patent Application No. 60/474,094, filed May 29, 2003, and U.S. Provisional Patent Application No. 60/509,752, filed Oct. 7, 2003, all of which are incorporated herein by reference in their entireties for all purposes.

BACKGROUND OF THE INVENTION

1. Field of the Invention

The present invention relates to branched water-soluble polymers and conjugates formed from these branched polymers.

2. Introduction

The conjugation of the hydrophilic polymers, such as poly(ethylene glycol), abbreviated PEG, also known as poly(ethylene oxide), abbreviated PEO, to molecules and surfaces is of considerable utility in biotechnology and medicine. In its most common form, PEG is a linear polymer terminated at each end with hydroxyl groups:

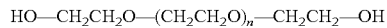

$$HO-CH_2CH_2O-(CH_2CH_2O)_n-CH_2CH_2-OH$$

where n typically ranges from about 3 to about 4000. Many end-functionalized derivatives are known in the literature and commercially available. See, for example, Shearwater Polymers, Inc. Catalog "Polyethylene Glycol Derivatives."

PEG species with a different group at each of the two termini are particularly useful compounds. For example, heterobifunctional PEGs are of use as cross-linking agents. Moreover, PEG molecules that are "capped" at one terminus, e.g., an alkyl group, such as methoxy allow the hydroxyl terminus of the molecule to be converted into any one of a large number of reactive organic functional groups.

Random or block copolymers of ethylene oxide and propylene oxide, shown below, are closely related to PEG in their chemistry, and they can be substituted for PEG in many of its applications.

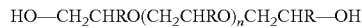

$$HO-CH_2CHRO(CH_2CHRO)_nCH_2CHR-OH$$

in which each R is independently H or $CH_3$.

The formation of conjugates between therapeutically active species and water-soluble polymers has proven a productive strategy for improving the pharmacokinetics and pharmacodynamics of therapeutic agents. See, for example, Dunn and Ottenbrite, "Polymeric Drugs and Drug Delivery Systems:" ACS Symposium Series 469, American Chemical Society, Washington, D.C. 1991. For example, the use of PEG to derivatize peptide therapeutics has been demonstrated to reduce the immunogenicity of the peptides and prolong the clearance time from the circulation. For example, U.S. Pat. No. 4,179,337 (Davis et al.) concerns non-immunogenic peptides, such as enzymes and peptide hormones coupled to polyethylene glycol (PEG) or polypropylene glycol. Between 10 and 100 moles of polymer are used per mole peptide and at least 15% of the physiological activity is maintained.

Many other examples of PEG-peptide conjugates are known in the art. The principal mode of attachment of PEG, and its derivatives, to peptides is a non-specific bonding through a peptide amino acid residue. For example, U.S. Pat. No. 4,088,538 discloses an enzymatically active polymer-enzyme conjugate of an enzyme covalently bound to PEG. Similarly, U.S. Pat. No. 4,496,689 discloses a covalently attached complex of α-1 protease inhibitor with a polymer such as PEG or methoxypoly(ethylene glycol) ("mPEG"). Abuchowski et al. (*J. Biol. Chem.* 252: 3578 (1977) discloses the covalent attachment of mPEG to an amine group of bovine serum albumin. WO 93/15189 (Veronese et al.) concerns a method to maintain the activity of polyethylene glycol-modified proteolytic enzymes by linking the proteolytic enzyme to a macromolecularized inhibitor. The conjugates are intended for medical applications. U.S. Pat. No. 4,414,147 discloses a method of rendering interferon less hydrophobic by conjugating it to an anhydride of a dicarboxylic acid, such as poly(ethylene succinic anhydride). PCT WO 87/00056 discloses conjugation of PEG and poly(oxyethylated) polyols to such proteins as interferon-β, interleukin-2 and immunotoxins. EP 154,316 discloses and claims chemically modified lymphokines, such as IL-2 containing PEG bonded directly to at least one primary amino group of the lymphokine. U.S. Pat. No. 4,055,635 discloses pharmaceutical compositions of a water-soluble complex of a proteolytic enzyme linked covalently to a polymeric substance such as a polysaccharide.

Another mode of attaching PEG to peptides is through the non-specific oxidation of glycosyl residues on a peptide. The oxidized sugar is utilized as a locus for attaching a PEG moiety to the peptide. For example M'Timkulu (WO 94/05332) discloses the use of a hydrazine- or amino-PEG to add PEG to a glycoprotein. The glycosyl moieties are randomly oxidized to the corresponding aldehydes, which are subsequently coupled to the amino-PEG.

In each of the methods described above, poly(ethyleneglycol) is added in a random, non-specific manner to reactive residues on a peptide backbone. Frequently, derivatization with PEG results in a loss of peptide activity that is directly attributable to the non-selective nature of the chemistries utilized to conjugate the water-soluble polymer.

Another difficulty associated with forming conjugates between water-soluble polymers and biomolecules is the ability of the reactive water-soluble polymer reagent to label the biomolecule at more than one site. Though it is often desirable to include more than one water-soluble polymer moiety per conjugate, the degree of diminution of biomolecule activity is often proportional to the number of polymer moieties bound to the biomolecule. Accordingly, there is interest in obtaining reactive, branched species that include two or more water-soluble polymer moieties per molecule. Through the use of branched molecules, more than one water-soluble polymer can be conjugated to a biomolecule without the necessity of interfering with more than one site on the biomolecule.

Branched polymers based upon poly(ethylene glycol) are known in the art. For example, Greenwald et al. (WO 98/41562) disclose a branched PEG that is based on a 1,3-diamino-2-propanol core. Morpurgo and co-workers discuss the use of branched PEG based on a lysine core is discussed in *Appl. Biochem. Biotechnol.* 56: 59-72 (1996). A similar lysine-based branched PEG was prepared by Guiotto et al., *Bioorg. Med. Chem. Lett* 12: 177-180 (2002). Harris et al. (U.S. Pat. No. 5,932,462) also prepared a branched PEG that is based upon lysine. Martinez et al. (U.S. Pat. No. 5,643,575) describe a number of branched PEG species that are based upon various core structures and the conjugation of these species with a biologically active material (U.S. Pat. No. 6,113,906).

Polymers, such as poly(ethylene glycol) are known to exist as heterodisperse populations, which include a range of polymer chain lengths and molecular weights. When preparing therapeutic formulations, it is clearly desirable to utilize polymers with minimal heterodispersity to ensure consistency and reproducibility between preparations. Few methods of preparing mono-disperse PEG samples are known in the art. Loiseau et al. have published a synthesis of well-defined PEG molecules. The method utilizes a protection/deprotection strategy that is less than optimal for the preparation of large quantities of substantially mono-disperse PEGs. Thus, in addition to branched poly(ethylene glycol) polymers, a method for preparing mono-disperse PEG and incorporating the mono-disperse material into the branched polymers would be highly desirable.

The present invention answers the need for both branched water-soluble polymers and mono-disperse PEG species, opening a route to new therapeutic conjugates, e.g., peptide conjugates, and addressing the need for more stable and therapeutically effective therapeutic species. There remains still a need for an industrially practical method for the modification of therapeutic biomolecules with modifying groups such as water-soluble polymers. Of particular interest are methods in which the conjugate has improved properties relative to the unmodified therapeutic agent. The present invention fulfills these and other needs.

BRIEF SUMMARY OF THE INVENTION

The present invention provides branched water-soluble polymers that are based on cores of diverse structure. The branched polymers of the invention provide a means to attach two or more water-soluble polymer moieties to another species through a single locus of attachment. The invention is illustrated by reference to branched PEG molecules. The focus on PEG as a representative water-soluble polymer is for clarity of illustration and should not be interpreted to limit the invention. Those of skill will appreciate that the branched species described herein can be prepared with essentially any water-soluble polymer. In addition to PEG, other exemplary water-soluble polymer include poly(propylene glycol).

In a first aspect, the invention provides a branched water-soluble polymer having the formula:

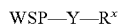

WSP—Y—R$^x$ in which WSP is a water-soluble polymer. The symbol Y represents a linker, e.g., a bond, or a moiety comprising an amide, carboxylic acid ester, urethane, mercaptan, substituted or unsubstituted alkyl, and the like. Exemplary linkers include: a bond, $(CH_2)_n$, $(CH_2)_mC(O)O(CH_2)_n$, $(CH_2)_mC(O)NH(CH_2)_n$, $(CH_2)_mC(O)NH(CH_2)_n$, $(CH_2)_mO(CH_2)_n$, $(CH_2)_m NH(CH_2)_n$ and $(CH_2)_mS(CH_2)_n$ in which m and n are integers independently selected from 0 to 6. $R^x$ is a water-soluble polymer, substituted or unsubstituted alkyl moiety linked to a water-soluble polymer; an amino acid or dimer of an amino acid linked to a water-soluble polymer; or a sugar or a sugar nucleotide linked to a water-soluble polymer. WSP and the water-soluble polymer component of $R^x$ may be the same water-soluble polymer or different water-soluble polymers.

Exemplary water-soluble polymers of use in the compounds of the invention include m-PEG, PEG, m-PPG, PPG, polysialic acid, polyglutamate, polyaspartate, polylysine, polyethyeleneimine, biodegradable polymers (e.g., polylactide, polyglyceride), and functionalized PEG, e.g., terminal-functionized PEG.

In an exemplary embodiment, Y is substituted alkyl and the invention provides a branched water-soluble polymer having the formula:

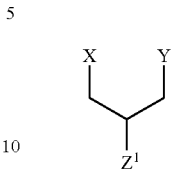

(I)

in which X and Y are members independently selected from $OR^1$, $NR^2R^3$, $SR^4$, $COOR^5$, $CONR^6R^7$, $OCONR^6R^7$, substituted and unsubstituted alkyl, and substituted and unsubstituted aryl. $Z^1$ is a member selected from $OR^{1'}$, $NR^{2'}R^{3'}$, $SR^{4'}$, $COOR^{5'}$, $CONR^{6'}R^{7'}$, substituted and unsubstituted alkyl, and substituted and unsubstituted aryl. The symbols $R^1$, $R^4$, and $R^5$ represent a water-soluble polymer. $R^2$, $R^3$, $R^6$, and $R^7$ are members independently selected from H, substituted and unsubstituted alkyl, substituted and unsubstituted aryl, substituted and unsubstituted heteroaryl, substituted and unsubstituted heterocycloalkyl, a reactive functional group, and a water-soluble polymer with the proviso that these groups are selected such that the compound according to Formula I includes at least two water-soluble polymer moieties. The symbols $R^{1'}$, $R^{2'}$, $R^{3'}$, $R^{4'}$, $R^{5'}$, $R^{6'}$, and $R^{7'}$ represent groups that are independently selected from H, substituted and unsubstituted alkyl, substituted and unsubstituted aryl, substituted and unsubstituted heteroaryl, substituted and unsubstituted heterocycloalkyl, a reactive functional group, a carrier molecule, and a water-soluble polymer.

In another exemplary embodiment, $Z^1$ comprises a saccharyl moiety. The saccharyl moiety can be an activated saccharyl moiety, e.g., a nucleotide sugar. Still further, $Z^1$ can comprise a saccharyl moiety that is directly bound to an amino acid of a peptide, or indirectly bound to an amino acid of a peptide by its conjugation to a glycosyl residue attached to the amino acid.

The invention also provides a branched polymer that is based on an amino acid or oligo-amino acid (e.g., di-, tri-, tetra-peptide). Exemplary amino acid-based branched polymers have a formula selected from:

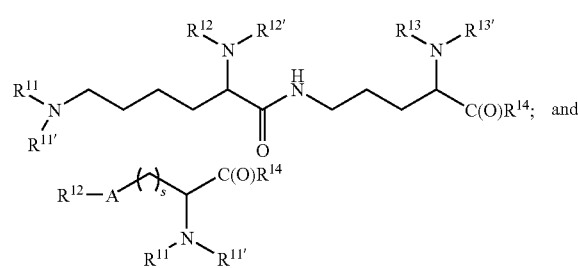

wherein $R^{11}$, $R^{11'}$, $R^{12}$, $R^{12'}$, $R^{13}$, $R^{13'}$ are independently selected from H, substituted or unsubstituted alkyl and water-soluble polymers, with the proviso that these groups are selected such that the compound set forth above includes at least two water-soluble polymer moieties. $R^{14}$ is a member selected from OH, reactive functional groups, a group comprising a saccharide moiety or a group that is linked to a carrier molecule. A is a member selected from NH, O and S. The index "s" represents and integer from 1 to 5.

Each of the compounds set forth in the formulae above are of use for the chemical PEGylation of another species (e.g., nucleic acid, peptide, saccharide, etc.). Methods of forming conjugates between PEG (and species containing PEG) are generally known in the art. See, for example, Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

In another exemplary embodiment, $R^{14}$ comprises a saccharyl moiety. The saccharyl moiety can be an activated saccharyl moiety, e.g., a nucleotide sugar. Still further, $R^{14}$ can comprise a saccharyl moiety that is directly bound to an amino acid of a peptide, or indirectly bound to an amino acid of a peptide by its conjugation to a glycosyl residue attached to the amino acid.

In yet another aspect, the invention provides a branched water-soluble polymer that is based upon a saccharide nucleus ("branch core"). Those of skill will appreciate that the saccharide nucleus can be of any structure. Exemplary saccharides of use in this aspect of the invention include GlcNAc, Gal, Sia, Fuc, Glc, GalNAc, $GalNH_2$, $GlcNH_2$ and the like.

An exemplary compound of the invention has the formula:

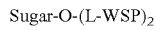

in which L is a linker and WSP is a water-soluble polymer.

In another exemplary embodiment, the saccharide-based branched water-soluble polymer of the invention has the formula:

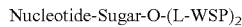

A further exemplary compound according to this aspect of the invention, which is based upon a sialic acid nucleus has the formula:

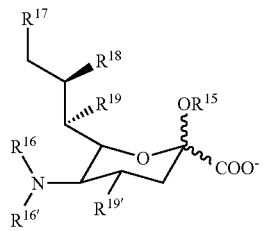

in which $R^{16}$ and $R^{16'}$ are members selected from H, acetyl, and:

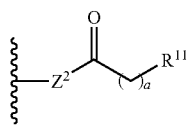

(I)

and $R^{17}$, $R^{18}$, $R^{19}$ and $R^{19'}$ are members independently selected from H, OH, $NH_2$, NHAc and the moiety according to Formula I. In Formula I, $Z^2$ is a member selected from O, S, $CH_2$ and S. $R^{11}$ is as described above, and the index "a" represents an integer from 0 to 20, with the proviso that at least two of $R^{16}$, $R^{16'}$, $R^{17}$, $R^{18}$ and $R^{19}$ have a structure according to Formula I. R11 can also be a group linked to a carrier molecule or a bond to a carrier molecule. $R^{15}$ is a member selected from H and activating groups, e.g., a nucleotide phosphate.

In another aspect, the branched polymer is based upon galactose or N-acetyl galactose and it has the formula:

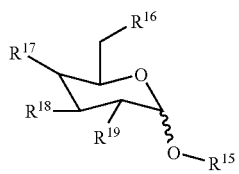

wherein $R^{15}$-$R^{19}$ are as described above and at least two of $R^{15}$-$R^{19}$ are a moiety according to Formula I.

Other exemplary sugar-derived structures having a formula such as that above are mannose and glucose-based branched water-soluble polymers.

Still further, $R^{15}$ can comprise a bond to an amino acid of a peptide or to a glycosyl moiety that is directly bound to an amino acid of a peptide, or indirectly bound to an amino acid of a peptide by its conjugation to a glycosyl residue attached to the amino acid.

The invention also provides a method of preparing an essentially mono-disperse population of poly(ethylene glycol) molecules. The method includes contacting a PEG molecule with a well-defined molecular weight, e.g., PEG200 with at least two equivalents of a bifunctional activated PEG that also has a well-defined molecular weight, e.g., PEG200, thereby producing a mono-disperse sample of a PEG, e.g., PEG600:

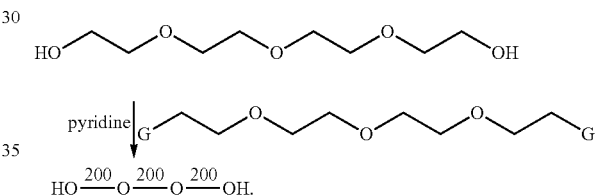

G is a leaving group, such as a sulfonate or tresylate ester. The mono-disperse sample of PEG600 can then be contacted with the bifunctional activated PEG200 to form a mono-disperse PEG100. Alternatively, the mono-disperse PEG600 can be converted to the corresponding bifunctional derivative and reacted with at least two equivalents of a mono-disperse di-hydroxy-PEG600, producing a mono-disperse PEG 1800. The process of the invention is repeated until a mono-disperse PEG of the desired size is obtained. The synthesis can be designed such that the molecular weight differences between the starting material and the product allow for the separation of any unreacted or partially reacted materials by size exclusion chromatography.

Moreover, in response to the need for improved methods of preparing modified water-soluble polymers, such as poly(ethylene glycol), the present invention provides methods for the chemical activation and elongation of the polymer backbone. The mono-activated PEG molecules are of use to conjugate PEG to a wide variety of species, e.g, targeting moieties, therapeutic moieties, anti-tumor drugs, cytotoxins, radioactive agents, amino acids, saccharides and the like.

Thus, in another aspect, the present invention provides a method for the step-wise assembly of activated water-soluble polymers, particularly poly(ethylene glycol) and its structural analogues. The method provides easy access to both mono- and bi-functionalized PEG molecules.

Thus, in an exemplary embodiment, the invention provides a method of preparing a derivative of poly(ethylene glycol). The method is outlined below:

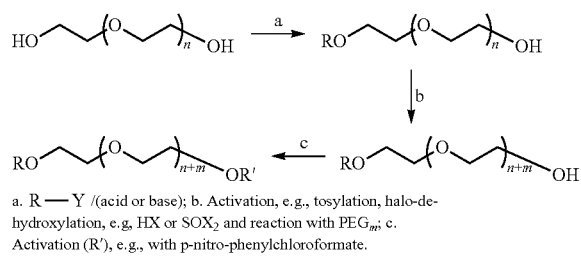

a. R—Y /(acid or base); b. Activation, e.g., tosylation, halo-de-hydroxylation, e.g, HX or SOX₂ and reaction with PEG$_m$; c. Activation (R'), e.g., with p-nitro-phenylchloroformate.

in which the indexes m and n independently represent integers from 1 to 100,000.

In step a, the starting glycol is contacted with an activated group (R—Y) that reacts with a hydroxyl moiety of the glycol. Y is generally a leaving group, allowing placement of R on one of the hydroxyl moieties of the PEG molecule. In step b, the free hydroxyl of the resulting adduct is activated by its conversion to a group such as a sulfonate ester. The activated PEG species is contacted with another PEG moiety of the same or different degree of polymerization as the starting PEG ("PEG$_m$"). To allow its attachment to another species, the RO-PEG$_{(n+m)}$ is optionally activated at the free hydroxyl moiety.

The compounds of the invention are of use in forming water-soluble polymer conjugates of a substrate, such as a therapeutic agent, e.g., peptides, lipids, glycolipids, through direct chemical PEGylation of one or more available reactive residue on the therapeutic agent. The compounds of the invention are also readily incorporated into activated sugar conjugates that can be utilized in enzymatically-mediated glyco-PEGylation of a substrate, e.g., a therapeutic agent.

The invention also provides pharmaceutical formulations of therapeutic agents to which are conjugated one or more branched water-soluble polymer of the invention. Also provided are methods of treating diseases that are ameliorated or cured by administration of a conjugate between a therapeutic agent and a branched water-soluble polymer of the invention.

Additional aspects, advantages and objects of the present invention will be apparent from the detailed description that follows.

BRIEF DESCRIPTION OF THE DRAWINGS

Detailed Description of the Invention

Abbreviations

PEG, poly(ethyleneglycol); m-PEG, methoxy-poly(ethylene glycol); PPG, poly(propyleneglycol); m-PPG, methoxy-poly(propylene glycol); Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Sia, sialic acid; and NeuAc, N-acetylneuraminyl.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "glycoconjugation," as used herein, refers to the enzymatically mediated conjugation of a modified sugar species to an amino acid or glycosyl residue of a peptide. A subgenus of "glycoconjugation" is "glyco-PEG-ylation," in which the modifying group of the modified sugar is poly (ethylene glycol), and alkyl derivative (e.g., m-PEG) or reactive derivative (e.g., H$_2$N-PEG, HOOC-PEG) thereof.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O—C$_1$-C$_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, Glycobiology 2: 25-40 (1992); Sialic Acids Chemistry, Metabolism and Function, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are petides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is glycoconjugated with a modified sugar as set forth herein. In a representative example, the peptide is a mutant peptide having an O-linked glycosylation site not present in the wild-type peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "modified sugar," refers to a naturally- or non-naturally-occurring carbohydrate, modified with a branched water-soluble polymer of the invention, that can be enzymatically added onto an amino acid or a glycosyl residue of a peptide, lipid, glycolipid and the like. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group," which is a branched polymer of the invention. The locus of functionalization with the modifying group is selected such that it does not prevent the "modified sugar" from being added enzymatically to a peptide or other substrate.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The terms "poly(ethylene glycol)", "PEG", "poly(propylene glycol)" and "PPG" are used in their generic sense and they also encompass derivatives of the parent compounds, e.g., mono-alkyl species, e.g., m-PEG, m-PPG, reactive species, N-hydroxysuccinimide, p-nitrophenylcarbonate (p-NP), HOBT derivatives, and amines. Also included within these terms are species that include two or more modifications, e.g., p-NP-PEG-OMe, and the like.

The term, "glycosyl linking group," as used herein refers to a glycosyl residue to which an agent (e.g., water-soluble polymer, therapeutic moiety, biomolecule) is covalently attached. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. An "intact glycosyl linking group" refers to a linking group that is derived from a glycosyl moiety in which the individual saccharide monomer that links the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

The terms "large-scale" and "industrial-scale" are used interchangeably and refer to a reaction cycle that produces at least about 250 mg, preferably at least about 500 mg and more preferably at least about 1 gram of glycoconjugate at the completion of a single reaction cycle.

The symbol  whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, Acc. Chem. Res. 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR$^1$, =O, =NR', —NR'R", —SR', -halogen, —SiR'R"R'", —OC(O)R', —C(O)R', —CO$_2$R$^1$, —CONR'R", —OC(O)NR'R", —NR"C(O)R', —NR'—C(O)NR"R'", —NR"C(O)$_2$R$^1$, —NR—C(NR'R"R'")=NR"", —NR—C(NR'R")=NR'", —S(O)R', —S(O)$_2$R$^1$, —S(O)$_2$NR'R", —NRSO$_2$R$^1$, —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR$^1$, =O, =NR', —NR'R", —SR', -halogen, —SiR'R"R'", —OC(O)R', —C(O)R', —CO$_2$R$^1$, —CONR'R", —OC(O)NR'R", —NR"C(O)R', —NR'—C(O)NR"R'", —NR"C(O)$_2$R$^1$, —NR—C(NR'R"R'")=NR"", —NR—C(NR'R")=NR'", —S(O)R', —S(O)$_2$R$^1$, —S(O)$_2$NR'R", —NRSO$_2$R$^1$, —CN and —NO$_2$, —R$^1$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or —N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counter ions.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "Linker" or "L", as used herein, refers to a single covalent bond or a series of stable covalent bonds incorporating 1-20 nonhydrogen atoms selected from the group consisting of C, N, O, S and P that covalently attach the water-soluble polymers or branched water-soluble polymers to another moiety such as a chemically reactive group or a conjugated substance including biological and non-biological substances. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a water-soluble polymer, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

"Non-covalent protein binding groups" are moieties that interact with an intact or denatured polypeptide in an associative manner. The interaction may be either reversible or irreversible in a biological milieu. The incorporation of a "non-covalent protein binding group" into a fluorogenic compound of the invention provides the compound with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxy late, boronate, sulfate, sulfone, thiosulfate, and thiosulfonate.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a quencher, a fluorophore or another moiety.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage resulting in a fluorescent or fluorogenic labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "targeting group" refers to a moiety that is: (1) able to actively direct the entity to which it is attached (e.g., a fluorogenic moiety) to a target region, e.g., a cell; or (2) is preferentially passively absorbed by or entrained within a target region. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly (ethers), dendrimers, poly(amino acids) and so forth.

"Carrier molecule," as used herein refers to any molecule to which a compound of the invention is attached. Representative carrier molecules include a protein (e.g., enzyme, antibody), glycoprotein, peptide, saccharide (e.g., mono-oliogo- and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism.

Introduction

The present invention provides branched water-soluble polymers and conjugates of the branched water-soluble polymers. The conjugates are formed between the branched water-soluble polymers of the invention and a species that includes a reactive group to which the branched water-soluble polymer can be conjugated. Exemplary conjugation partners for the water-soluble polymers of the invention include peptides, glycopeptides, lipids and glycolipids. An exemplary conjugate is one in which a modified sugar bearing a branched water-soluble polymer of the invention is attached either directly or indirectly (e.g., through an intervening glycosyl residue) to a glycosylation site on a peptide. Also provided are methods for producing the conjugates of the invention.

The conjugates and methods of forming the conjugates of the invention are illustrated herein by reference to peptide and glycopeptide conjugates. The focus of the discussion is for clarity of illustration and it should not be interpreted as limiting the utility of the branched water-soluble polymers disclosed herein to use in the formation of such conjugates. Those of skill in the art will recognize that the branched water-soluble polymers of the present invention are of use in forming a wide variety of branched water-soluble polymer conjugates.

As discussed in the preceding section, art-recognized chemical methods of covalent PEGylation rely on chemical conjugation through reactive groups on amino acids or carbohydrates. Through careful design of the conjugate and the reaction conditions, useful conjugates have been prepared using chemically-mediated conjugation strategies. A major shortcoming of chemical conjugation of polymers to proteins or glycoproteins is the lack of selectivity of the activated polymers, which often results in attachment of polymers at sites implicated in protein or glycoprotein bioactivity. Several strategies have been developed to address site selective conjugation chemistries, however, only one universal method suitable for a variety of recombinant proteins has been developed.

In contrast to art-recognized methods, the present invention provides a novel strategy for highly selective site directed glycoconjugation of branched water-soluble polymers, e.g., glyco-PEGylation. In an exemplary embodiment of the invention, site directed attachment of branched water-soluble polymers is accomplished by in vitro enzymatic glycosylation of specific peptide sequences. Glyco-conjugation can be performed enzymatically utilizing a glycosyltransferase, e.g., a sialyltransferase, capable of transferring the species branched water-soluble polymer-glycosyl, e.g., PEG-sialic acid, to a glycosylation site ("glyco-PEGylation").

Branched Water-Soluble Polymers

In a first aspect, the invention provides a branched water-soluble polymer having the formula:

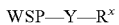

in which WSP is a water-soluble polymer. The symbol Y represents a linker, e.g., a bond, or a moiety comprising an amide, carboxylic acid ester, urethane, mercaptans, substituted or unsubstituted alkyl, and the like. Exemplary linking groups include a bond, $(CH_2)_n$, $(CH_2)_mC(O)O(CH_2)_n$, $(CH_2)_m C(O)NH(CH_2)_n$, $(CH_2)_m OC(O)NH(CH_2)_n$, $(CH_2)_m O(CH_2)_n$, $(CH_2)_mNH(CH_2)_n$ and $(CH_2)_mS(CH_2)_n$ in which m and n are integers independently selected from 0 to 6. $R^x$ is a substituted or unsubstituted alkyl moiety linked to a water-soluble polymer; an amino acid or dimer of an amino acid linked to a water-soluble polymer; or a sugar or a sugar nucleotide linked to a water-soluble polymer. WSP and the water-soluble polymer component of $R^x$ may be the same water-soluble polymer or different water-soluble polymers.

Exemplary water-soluble polymers of use in the compounds of the invention include m-PEG, PEG, m-PPG, PPG, polysialic acid, polyglutamate, polyaspartate, polylysine, polyethyeleneimine, polylactide, polyglyceride, and functionalized PEG, e.g., terminal-functionized PEG.

In an exemplary embodiment, Y is substituted alkyl and the invention provides a branched water-soluble polymer having the formula:

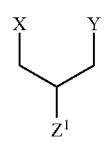

(I)

in which X and Y are members independently selected from $OR^1$, $NR^2R^3$, $SR^4$, $COOR^5$, $CONR^6R^7$, $OCONR^6R^7$, substituted and unsubstituted alkyl, and substituted and unsubstituted aryl. $Z^1$ is a member selected from $OR^{1'}$, $NR^{2'}R^{3'}$, $SR^{4'}$, $COOR^{5'}$, $CONR^{6'}R^{7'}$, substituted and unsubstituted alkyl, and substituted and unsubstituted aryl. The symbols $R^1$, $R^4$, and $R^5$ represent a water-soluble polymer. $R^2$, $R^3$, $R^6$, and $R^7$ are members independently selected from H, substituted and unsubstituted alkyl, substituted and unsubstituted aryl, substituted and unsubstituted heteroaryl, substituted and unsubstituted heterocycloalkyl, a reactive functional group, and a water-soluble polymer with the proviso that these groups are selected such that the compound according to Formula I includes at least two water-soluble polymer moieties. The symbols $R^{1'}$, $R^{2'}$, $R^{3'}$, $R^{4'}$, $R^{5'}$, $R^{6'}$, and $R^{7'}$ represent groups that are independently selected from H, substituted and unsubstituted alkyl, substituted and unsubstituted aryl, substituted and unsubstituted heteroaryl, substituted and unsubstituted heterocycloalkyl, a reactive functional group, a carrier molecule, and a water-soluble polymer.

In another exemplary embodiment, $Z^1$ comprises a saccharyl moiety. The saccharyl moiety can be an activated saccharyl moiety, e.g., a nucleotide sugar. Still further, $Z^1$ can comprise a saccharyl moiety that is directly bound to an amino acid of a peptide, or indirectly bound to an amino acid of a peptide by its conjugation to a glycosyl residue attached to the amino acid.

Exemplary compounds of the invention according to Formula I are set forth below:

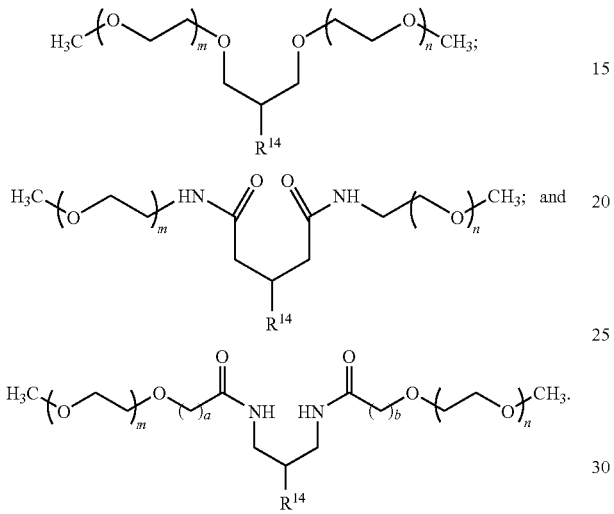

in which $R^{14}$ is OH or a reactive functional group. An exemplary reactive functional group is C(O)Q', in which Q' is selected such that C(O)Q' is a reactive functional group. Q' can also comprise a carrier molecule ("Ligand"). Exemplary species for Q' include halogen, NHS, pentafluorophenyl, HOBT, HOAt, and p-nitrophenyl. The index "m" and the index "n" are integers independently selected from 1 to 20,000.

The compounds set forth above, and additional compounds of the invention are readily prepared from such starting materials as:

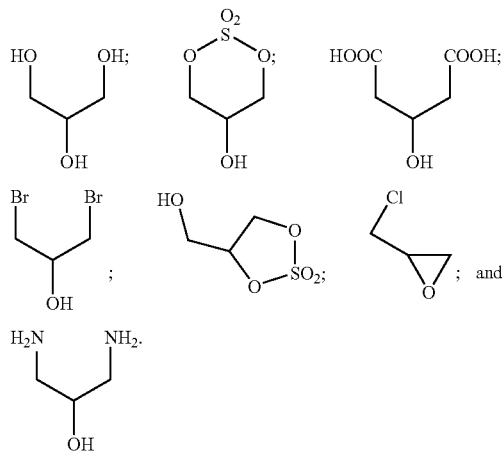

An exemplary route to a compound of the invention is set forth below:

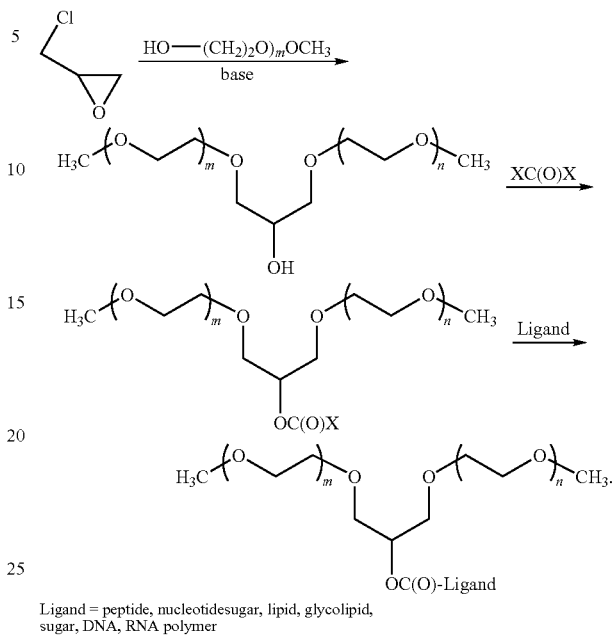

Ligand = peptide, nucleotidesugar, lipid, glycolipid, sugar, DNA, RNA polymer

Another exemplary route to compounds of the invention is set forth below:

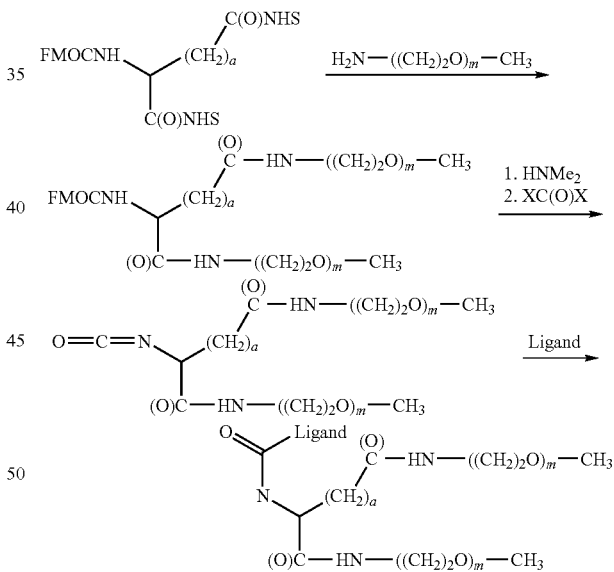

The invention also provides a branched polymer that is based on an amino acid or oligo-amino acid (e.g., di-, tri-, tetra-peptide). Exemplary amino acid-based branched polymers have a formula selected from:

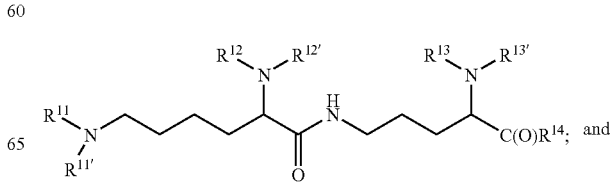

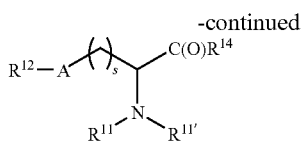

wherein $R^{11}$, $R^{11'}$, $R^{12}$, $R^{12'}$, $R^{13}$ and $R^{13'}$ are independently selected from H, substituted or unsubstituted alkyl and water-soluble polymers, with the proviso that these groups are selected such that the compound set forth above includes at least two water-soluble polymer moieties. $R^{14}$ is a member selected from OH, reactive functional groups, a group comprising a saccharide moiety or a group that is linked to a carrier molecule. A is a member selected from O and S. The index "s" represents and integer from 1 to 5. A is a member selected from NH, O and S.

Each of the compounds set forth in the formulae above are of use for the chemical PEGylation of another species (e.g., nucleic acid, peptide, saccharide, etc.). Methods of forming conjugates between PEG (and species containing PEG) are generally known in the art. See, for example, Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

In another exemplary embodiment, $R^{14}$ comprises a saccharyl moiety. The saccharyl moiety can be an activated saccharyl moiety, e.g., a nucleotide sugar. Still further, $R^{14}$ can comprise a saccharyl moiety that is directly bound to an amino acid of a peptide, or indirectly bound to an amino acid of a peptide by its conjugation to a glycosyl residue attached to the amino acid.

Exemplary compositions of the invention include:

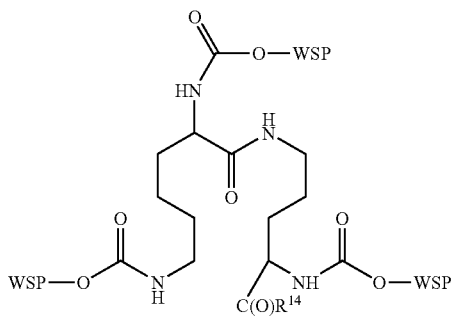

such as:

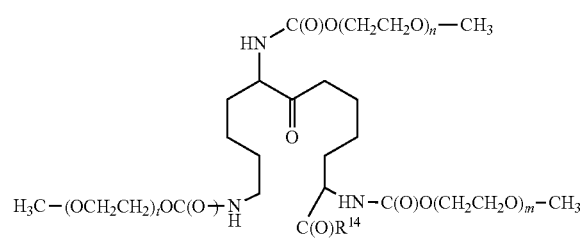

in which "m", "n" and "t" are integers independently selected from 1 to 20,000; and $R^{14}$ is as discussed above.

Other exemplary compounds include:

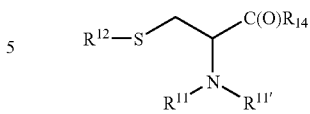

such as:

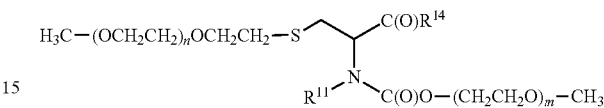

Additional compositions based upon amino acid structures are set forth in the table below.

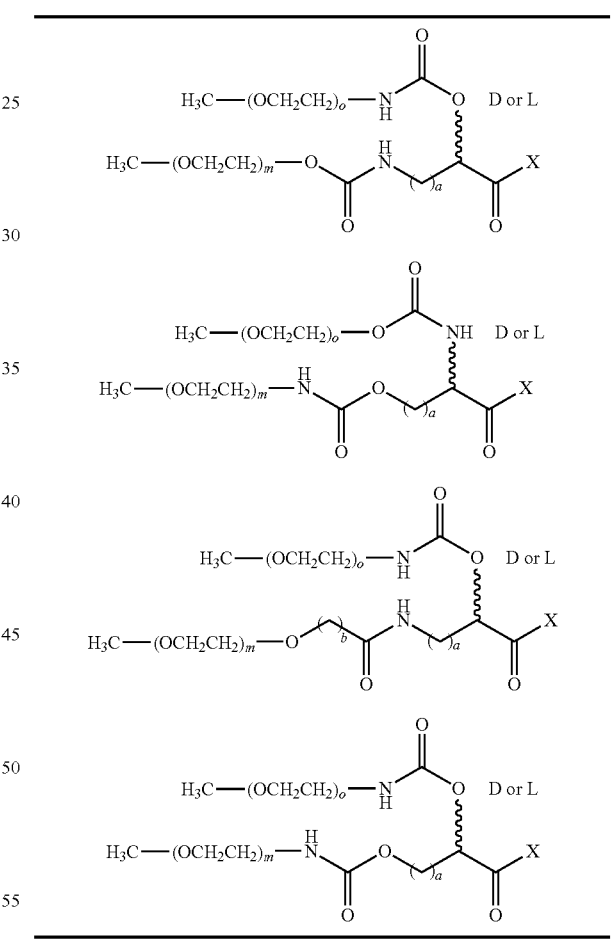

In the figures set forth in the table above the symbols a and b independently represent numbers between 1 and 10. The symbols m and o independently represent numbers between 1 and 10,000. The symbol X represents OH, H, Q (an activating group), and a biological moiety, such as a protein, sugar, lipid, or nucleotide.

In another exemplary embodiment, $R^{14}$ comprises a saccharyl moiety. The saccharyl moiety can be an activated saccharyl moiety, e.g., a nucleotide sugar. Still further, $R^{14}$ can comprise a saccharyl moiety that is directly bound to an amino acid of a peptide, or indirectly bound to an amino acid of a peptide by its conjugation to a glycosyl residue attached to the amino acid.

In yet another aspect, the invention provides a branched water-soluble polymer that is based upon a saccharide nucleus ("branch core"). Those of skill will appreciate that the saccharide nucleus can be of any structure. Exemplary saccharides of use in this aspect of the invention include GlcNAc, Gal, Sia, Fuc, Glc, GalNAc, GalNH$_2$, GlcNH$_2$ and the like.

An exemplary compound of the invention has the formula:

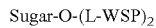
Sugar-O-(L-WSP)$_2$ in which L is a linker and WSP is a water-soluble polymer.

A further exemplary compound of the invention has the formula:

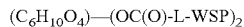
(C$_6$H$_{10}$O$_4$)—(OC(O)-L-WSP)$_2$ in which C$_6$H$_{10}$O$_4$ is a saccharide branch core in which two of the saccharide OH moieties are converted to OC(O)-linker-WSP.

Yet another exemplary compound of the invention has the formula:

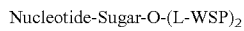
Nucleotide-Sugar-O-(L-WSP)$_2$

In another exemplary embodiment, the saccharide-based branched water-soluble polymer of the invention has the formula:

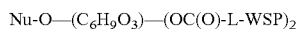
Nu-O—(C$_6$H$_9$O$_3$)—(OC(O)-L-WSP)$_2$ in which Nu is a nucleotide.

A further exemplary compound according to this aspect of the invention, which is based upon sialic acid nucleus has the formula:

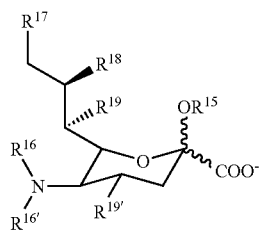

in which R$^{16}$ and R$^{16'}$ are members selected from H, acetyl, and:

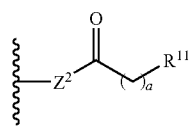
(I)

and R$^{17}$, R$^{18}$, R$^{19}$ and R$^{19'}$ are members independently selected from H, OH, NH$_2$, NHAc and the moiety according to Formula I. In Formula I, Z$^2$ is a member selected from O, S, CH$_2$ and S. R$^{11}$ is as described above, and the index "a" represents an integer from 0 to 20, with the proviso that at least two of R$^{16}$, R$^{16'}$, R$^{17}$, R$^{18}$ and R$^{19}$ have a structure according to Formula I. R$^{11}$ can also be a group linked to a carrier molecule or a bond to a carrier molecule. R$^{15}$ is a member selected from H and activating groups, e.g., a nucleotide phosphate.

In another exemplary embodiment, the linker of Formula I has the structure:

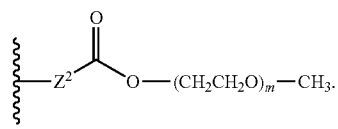

In yet another exemplary embodiment, the linker of Formula I has the structure:

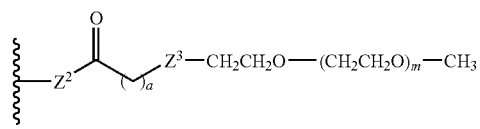

in which Z$^3$ is a member selected from NH, O and S.

In an exemplary embodiment, Z$^2$ is NH.

In another aspect, the branched polymer is based upon galactose or N-acetyl galactose and it has the formula:

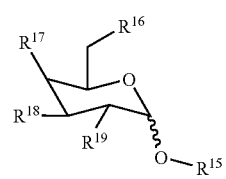

wherein R$^{15}$-R$^{19}$ are as described above and at least two of R$^{15}$-R$^{19}$ are a moiety according to Formula I.

Still further, R$^{15}$ can comprise a bond to an amino acid of a peptide or to a glycosyl moiety that is directly bound to an amino acid of a peptide, or indirectly bound to an amino acid of a peptide by its conjugation to a glycosyl residue attached to the amino acid.

An exemplary scheme for preparing the branched saccharide core water-soluble polymers of the invention is provided below:

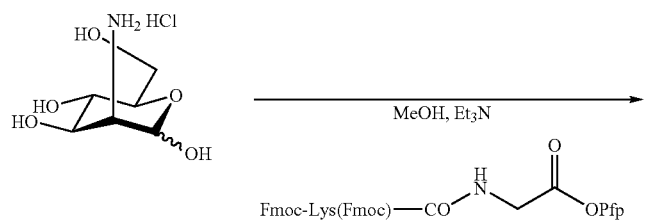
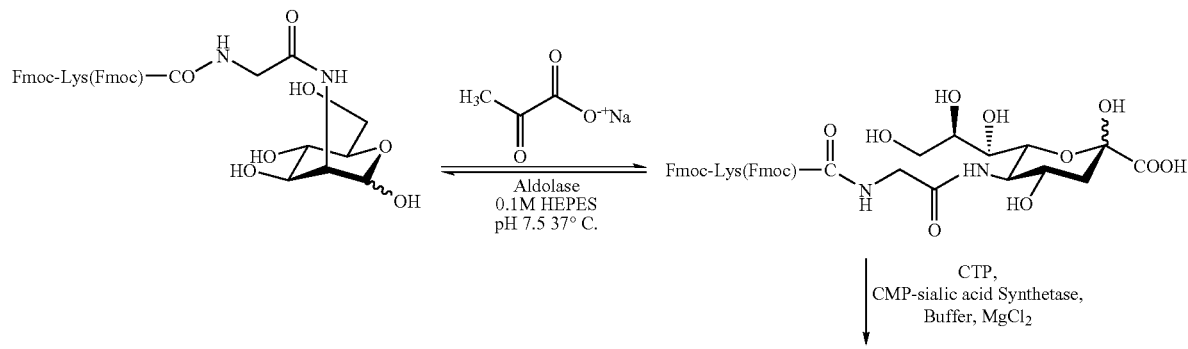
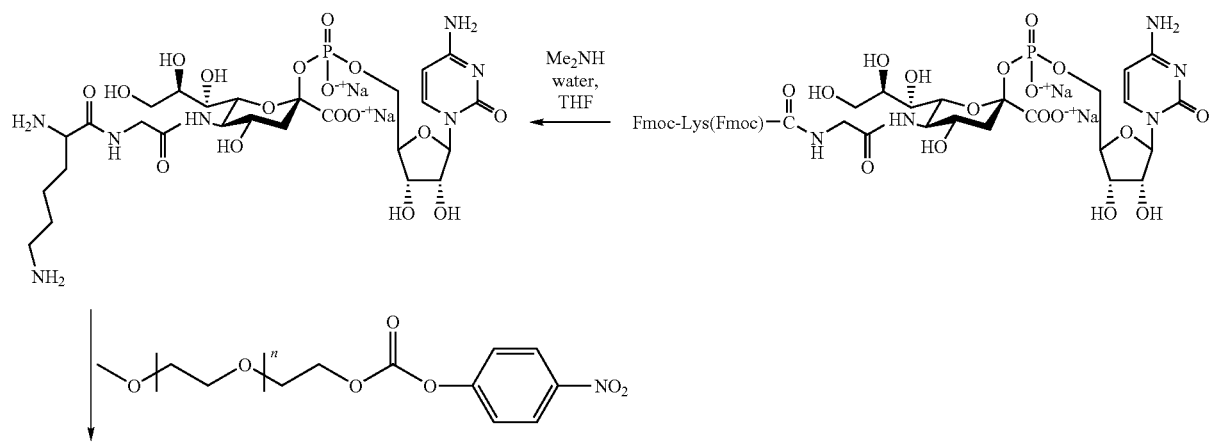
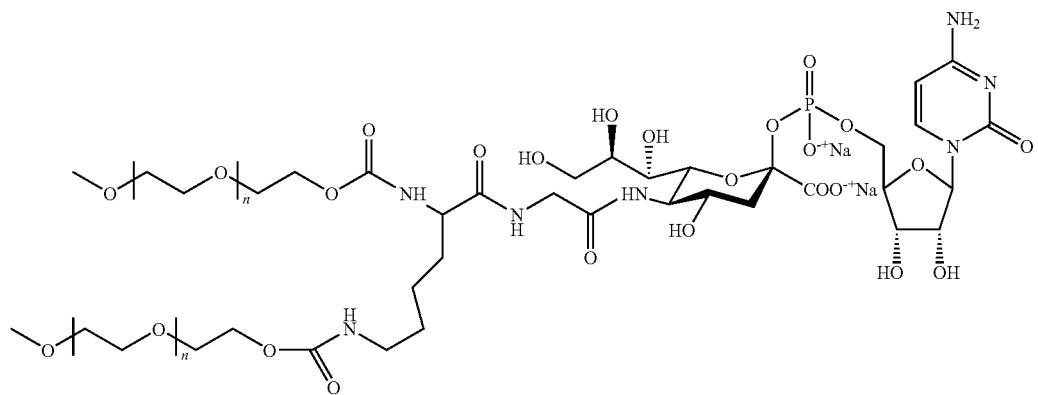

Another exemplary scheme for preparing the saccharide core branched water-soluble polymers of the invention is set forth below:

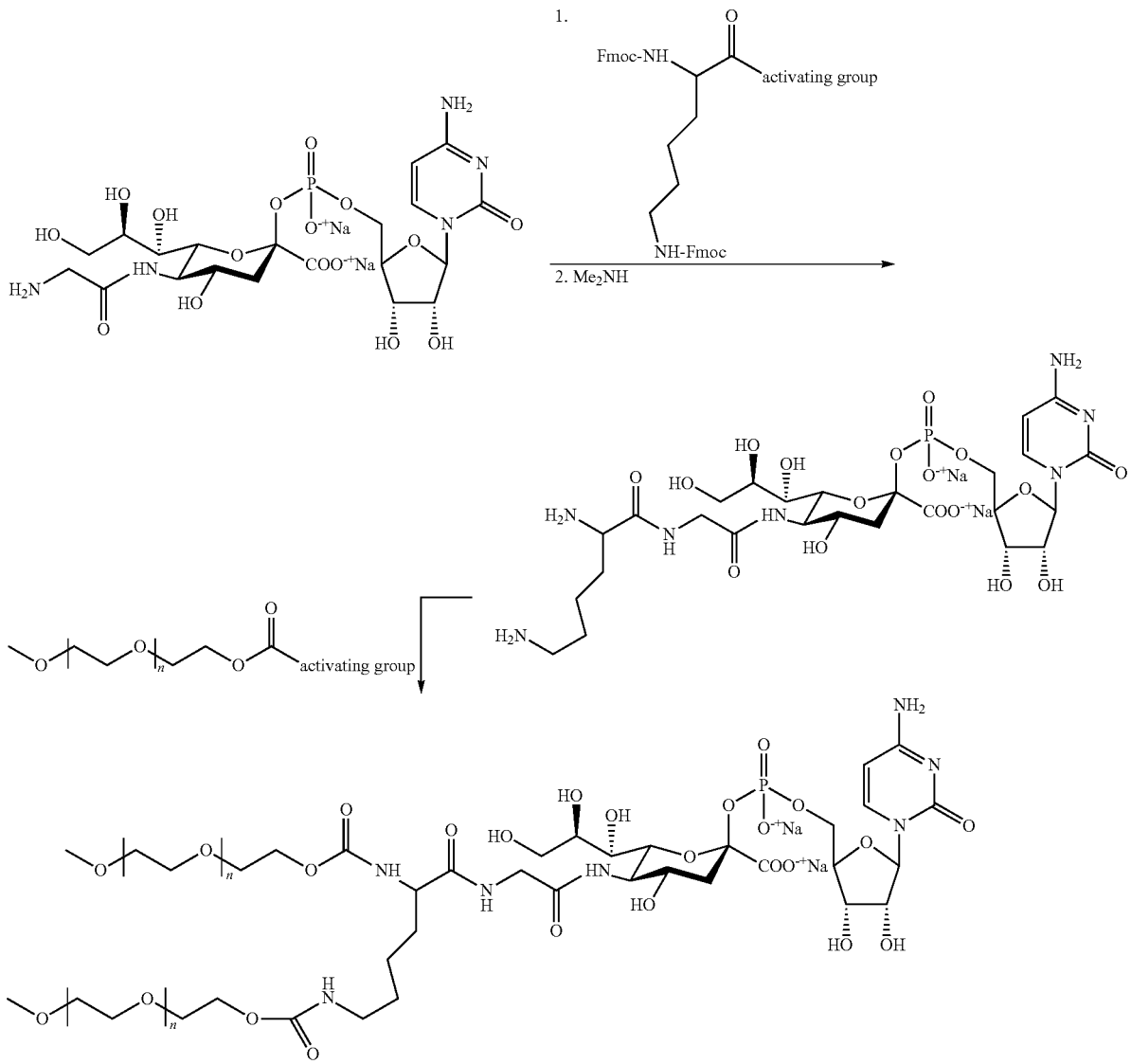

Mono-Dispersed Poly(Ethylene Glycol)

The invention also provides a mono-dispersed high molecular weight PEG and a method of preparing an essentially mono-disperse population of poly(ethylene glycol) molecules. The method includes contacting a PEG molecule with a well-defined molecular weight, e.g., PEG200 with at least two equivalents of a bifunctional activated PEG that also has a well-defined molecular weight, e.g., PEG200, thereby producing a mono-disperse sample of a PEG, e.g., PEG600:

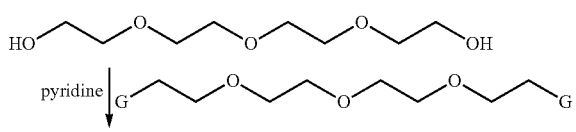

-continued

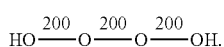

G is a leaving group, such as a sulfonate or tresylate ester. The mono-disperse sample of PEG600 can then be contacted with the bifunctional activated PEG200 to form a mono-disperse PEG100. Alternatively, the mono-disperse PEG600 can be converted to the corresponding bifunctional derivative and reacted with at least two equivalents of a mono-disperse di-hydroxy-PEG600, producing a mono-disperse PEG 1800. The process of the invention is repeated until a mono-disperse PEG of the desired size is obtained. The synthesis can be designed such that the molecular weight differences between the starting material and the product allow for the separation of any unreacted or partially reacted materials by size exclusion chromatography.

Moreover, in response to the need for improved methods of preparing modified water-soluble polymers, such as poly(ethylene glycol), the present invention provides methods for the chemical activation and elongation of the polymer backbone. The mono-activated PEG molecules are of use to conjugate PEG to a wide variety of species, e.g, targeting moieties, therapeutic moieties, anti-tumor drugs, cytotoxins, radioactive agents, amino acids, saccharides and the like.

Thus, in another aspect, the present invention provides a method for the step-wise assembly of activated water-soluble polymers, particularly poly(ethylene glycol) and its structural analogues. The method provides easy access to both mono- and bi-functionalized PEG molecules.

In step a, the starting glycol is contacted with an activated group (R—Y) that reacts with a hydroxyl moiety of the glycol. Y is generally a leaving group, allowing placement of R on one of the hydroxyl moieties of the PEG molecule. In step b, the free hydroxyl of the resulting adduct is activated by its conversion to a group such as a sulfonate ester. The activated PEG species is contacted with another PEG moiety of the same or different degree of polymerization as the starting PEG ("$PEG_m$"). To allow its attachment to another species, the $RO-PEG_{(n+m)}$ is optionally activated at the free hydroxyl moiety.

The mono-disperse PEGs of the invention are readily activated by art-recognized methods and the activated derivatives can be used to form conjugates. Alternatively, the mono-disperse PEG is incorporated into a branched PEG of the invention, which is used to form a conjugate.

Water-Soluble Polymers

The hydrophilicity of a selected peptide is enhanced by conjugation with polar molecules such as amine-, ester-, hydroxyl- and polyhydroxyl-containing molecules. Representative examples include, but are not limited to, polylysine, polyethyleneimine, and polyethers, e.g., poly(ethyleneglycol), m-poly(ethylene glycol), poly(propyleneglycol), m-poly(ethylene glycol), and other O-alkyl poly(alkylene glycol) moieties. Preferred water-soluble polymers are essentially non-fluorescent, or emit such a minimal amount of fluorescence that they are inappropriate for use as a fluorescent marker in an assay. Moreover, it is generally preferred to use polymers that are not naturally occurring sugars. An exception to this preference is the use of an otherwise naturally occurring sugar that is modified by covalent attachment of another entity (e.g., poly(ethylene glycol), poly(propylene glycol), biomolecule, therapeutic moiety, diagnostic moiety, etc.). In another exemplary embodiment, a therapeutic sugar moiety is conjugated to a linker arm and the sugar-linker arm cassette is subsequently conjugated to a peptide via a method of the invention.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Many water-soluble polymers are known to those of skill in the art and are useful in practicing the present invention. The term water-soluble polymer encompasses species such as saccharides (e.g., dextran, amylose, hyaluronic acid, poly (sialic acid), heparans, heparins, etc.); poly(amino acids); nucleic acids; synthetic polymers (e.g., poly(acrylic acid), poly(ethers), e.g., poly(ethylene glycol)); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "mono-disperse."

The present invention is further illustrated by reference to a poly(ethylene glycol) or monomethoxy-poly(ethylene glycol) (m-PEG) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002).

The poly(ethylene glycol) useful in forming the conjugate of the invention is either linear or branched. PEG moieties of any molecular weight, e.g., 5 Kd, 10 Kd, 20 Kd and 30 kD are of use in the present invention.

Reactive Functional Groups

The use of reactive derivatives of PEG (or other linkers) to attach one or more peptide moieties to the linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.,* 7: 175-186 (1984); Abuchowski et al., *J. Biol. Chem.,* 252: 3582-3586 (1977); Jackson et al., *Anal. Biochem.,* 165: 114-127 (1987); Koide et al., *Biochem Biophys. Res. Commun.,* 111: 659-667 (1983)), tresylate (Nilsson et. al., *Methods Enzymol.,* 104: 56-69 (1984); Delgado et al., *Biotechnol. Appl. Biochem.,* 12: 119-128 (1990)); N-hydroxysuccinimide derived active esters (Buckmann et al., *Makromol. Chem.,* 182: 1379-1384 (1981); Joppich et al., *Makromol. Chem.,* 180: 1381-1384 (1979); Abuchowski et al., *Cancer Biochem. Biophys.,* 7: 175-186 (1984); Katre et al. *Proc. Natl. Acad. Sci. U.S.A.,* 84: 1487-1491 (1987); Kitamura et al., *Cancer Res.,* 51: 4310-4315 (1991); Boccu et al., *Z. Naturforsch.,* 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.,* 15: 100-114 (1992); Veronese et al., *Appl. Biochem. Biotech.,* 11: 141-152 (1985)), imidazolyl formates (Beauchamp et al., *Anal. Biochem.,* 131: 25-33 (1983); Berger et al.,

*Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to, e.g., esters, ethers, aldehydes, etc.
(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be, for example, converted to disulfides or reacted with acyl halides;
(h) amine or sulfhydryl groups, which can be, for example, acylated, alkylated or oxidized;
(i) alkenes, which can undergo, for example, cycloadditions, acylation, Michael addition, etc; and
(j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Peptide Conjugates

The use of the compounds of the invention is exemplified by their use in forming peptide conjugates of branched water-soluble polymers. The focus of the discussion is for clarity of illustration. Those of skill will appreciate that the discussion is relevant to the formation of a variety of conjugates using the branched water-soluble polymers of the invention. In an exemplary embodiment, a chemically reactive branched water-soluble polymer is conjugated to a complementary reactive group on the peptide by a method known in the art or a modification thereof.

In another exemplary embodiment, the branched water-soluble polymer includes a saccharide moiety as the branch core or, alternatively, the branched water-soluble polymer is attached to a saccharide. The saccharide is a substrate for an enzyme that transfers the saccharide-based branched water-soluble polymer (or the saccharide-branched water-soluble polymer conjugate) onto an amino acid or glycosyl residue of the peptide. Those of skill in the art will appreciate that the methods set forth above are not limited to practice with peptides but are widely applicable to other species, e.g., lipids, glycolipids, saccharides and other therapeutic moieties.

The conjugates of the invention are formed by the enzymatic attachment of a branched water-soluble polymer-modified sugar to a glycosylated or an unglycosylated peptide. The modified sugar is directly added to a glycosylation site, or to a glycosyl residue attached either directly or indirectly (e.g., through one or more glycosyl residue) to a glycosylation site.

The branched water-soluble polymer-modified sugar, when interposed between the peptide (or glycosyl residue) and the modifying group on the sugar becomes what is referred to herein as "a glycosyl linking group." The glycosyl linking group can be "intact", or it may be altered during the attachment of the branched water-soluble polymer to the sugar, e.g., oxidized and reductively aminated. Using the exquisite selectivity of enzymes, such as glycosyltransferases, the present method provides peptides that bear a branched water-soluble polymer at one or more specific locations. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention.

In contrast to known chemical and enzymatic peptide elaboration strategies, the invention provides peptide- and glycopeptide-conjugates that have a substantially homogeneous derivatization pattern; the enzymes used in the invention are generally selective for a particular amino acid residue or combination of amino acid residues of the peptide. The conjugates of the invention can also be prepared using on a large-scale. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The branched water-soluble polymer conjugates of peptides are generally characterized as having increased therapeutic half-life due to, for example, reduced clearance rate, or reduced rate of uptake by the immune or reticuloendothelial system (RES). Moreover, antigenic determinants on the peptide component of the conjugates of the invention are masked by the branched water-soluble polymer, reducing or eliminating a host immune response to the peptide. Selective attachment of targeting agents to a peptide using an appropriate modified sugar can also be used to target a peptide to a particular tissue or cell surface receptor that is specific for the particular targeting agent.

The in vivo half-life of therapeutic glycopeptides can also be enhanced with branched water-soluble polymers that include polyethylene glycol (PEG, m-PEG) and polypropylene glycol (PPG). For example, chemical modification of proteins with branched PEG (PEG-ylation, m-PEG-ylation) increases their molecular size and decreases their surface- and functional group-accessibility, each of which are dependent on the size of the PEG attached to the protein. Modification of peptides with water-soluble polymers is generally recognized as a promising strategy for improving plasma half-lives and in proteolytic-stability, and a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). PEGylation of interleukin-2 has been reported to increase its antitumor potency in vivo (Katre et al. *Proc. Natl. Acad. Sci. USA.* 84: 1487-1491 (1987)) and PEG-ylation of a $F(ab')_2$ derived from the monoclonal antibody A7 has improved its tumor localization (Kitamura et al. *Biochem. Biophys. Res. Commun.* 28: 1387-1394 (1990)). Thus, in another preferred embodiment, the in vivo half-life of a peptide derivatized with a water-soluble polymer by a method of the invention is increased relevant to the in vivo half-life of the non-derivatized peptide.

The increase in peptide in vivo half-life of conjugates of the invention is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

In an exemplary embodiment, the link between the peptide and the selected moiety includes an intact glycosyl linking group interposed between the peptide and the water-soluble polymer. As discussed herein, attachment of the water-soluble polymer to a sugar moiety (or the use of a sugar branch core) provides a "modified sugar" that is recognized by an appropriate transferase enzyme, which appends the modified sugar onto the peptide. The saccharide component of the modified sugar, when interposed between the peptide and a selected moiety, becomes a "glycosyl linking group," e.g., an "intact glycosyl linking group." The glycosyl linking group is formed from any mono- or oligo-saccharide that, after modification with a water-soluble polymer, is a substrate for an appropriate transferase.

The conjugates of the invention will typically correspond to the general structure:

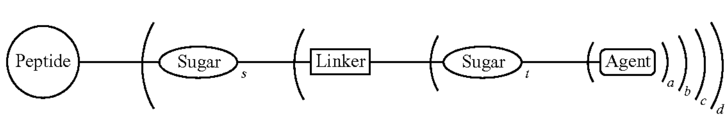

in which the symbols a, b, c, d and s represent a positive, non-zero integer; and t is either 0 or a positive integer. The "agent" is a branched water-soluble polymer of the invention. Alternatively, the sugar-agent is provided by a branched water-soluble polymer based on a saccharide branch core. The linker can be any of a wide array of linking groups, infra. Alternatively, the linker may be a single bond or a "zero order linker." The identity of the peptide is without limitation.

In an exemplary embodiment, the water-soluble polymer is PEG, m-PEG, PPG, or m-PPG, and the branched water-soluble polymer is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which the glycosyl linking group (e.g., GalNAc) is attached to an amino acid residue (e.g., Thr or Ser).

In addition to providing conjugates that are formed through an enzymatically added intact glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to a structurally identical amino acid or glycosyl residue. Thus, in a second aspect, the invention provides a peptide conjugate having a population of branched water-soluble polymer moieties, which are covalently bound to the peptide through a glycosyl linking group, e.g., an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of branched water-soluble polymer moieties covalently bound thereto through an intact glycosyl linking group. In a preferred embodiment, essentially every member of the population of branched water soluble polymer moieties is bound to an amino acid residue of the peptide via an intact glycosyl linking group, and each amino acid residue having an intact glycosyl linking group attached thereto has the same structure.

The present invention also provides conjugates analogous to those described above in which the peptide is further conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer.

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), IL-2 and IFN-α.

In exemplary embodiments, the conjugate is formed between a branched water-soluble polymer and a glycosylated or non-glycosylated peptide. The polymer, therapeutic moiety or biomolecule is conjugated to the peptide via an intact glycosyl linking group, which is interposed between, and covalently linked to both the peptide and the modifying group (e.g. water-soluble polymer). The method includes contacting the peptide with a mixture containing a modified sugar and a glycosyltransferase for which the modified sugar is a substrate. The reaction is conducted under conditions sufficient to form a covalent bond between the modified sugar and the peptide. The sugar moiety of the modified sugar is preferably selected from nucleotide sugars, activated sugars and sugars, which are neither nucleotides nor activated.

The acceptor peptide (glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more consensus glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Exemplary peptides components of the conjugates of the invention are set forth in Table 1.

TABLE 1

| Hormones and Growth Factors |
| --- |
| G-CSF |
| GM-CSF |
| M-CSF |
| TPO |
| EPO |
| EPO variants |
| alpha-TNF |
| Leptin |
| Enzymes and Inhibitors |
| t-PA |
| t-PA variants |
| Urokinase |
| Factors VII, VIII, IX, X |
| Dnase |
| Glucocerebrosidase |
| Hirudin |
| α1 antitrypsin |
| Antithrombin III |
| Cytokines and Chimeric Cytokines |
| Interleukin-1 (IL-1), 1B, 2, 3, 4 |
| Interferon-alpha (IFN-alpha) |
| IFN-alpha-2b |
| IFN-beta |
| IFN-gamma |
| Chimeric diptheria toxin-IL-2 |
| Receptors and Chimeric Receptors |

TABLE 1-continued

| |
| --- |
| CD4 |
| Tumor Necrosis Factor (TNF) receptor |
| Alpha-CD20 |
| MAb-CD20 |
| MAb-alpha-CD3 |
| MAb-TNF receptor |
| MAb-CD4 |
| PSGL-1 |
| MAb-PSGL-1 |
| Complement |
| GlyCAM or its chimera |
| N-CAM or its chimera |
| Monoclonal Antibodies (Immunoglobulins) |
| MAb-anti-RSV |
| MAb-anti-IL-2 receptor |
| MAb-anti-CEA |
| MAb-anti-platelet IIb/IIIa receptor |
| MAb-anti-EGF |
| MAb-anti-Her-2 receptor |
| Cells |
| Red blood cells |
| White blood cells (e.g., T cells, B cells, dendritic cells, macrophages, NK cells, neutrophils, monocytes and the like |
| Stem cells |

Other exemplary peptides components of conjugates of the invention include members of the immunoglobulin family (e.g., antibodies, MHC molecules, T cell receptors, and the like), intercellular receptors (e.g., integrins, receptors for hormones or growth factors and the like) lectins, and cytokines (e.g., interleukins). Additional examples include tissue-type plasminogen activator (t-PA), renin, clotting factors such as factors V-XII, bombesin, thrombin, hematopoietic growth factor, colony stimulating factors, viral antigens, complement proteins, α1-antitrypsin, erythropoietin, P-selectin glycopeptide ligand-1 (PSGL-1), granulocyte-macrophage colony stimulating factor, anti-thrombin III, interleukins, interferons, proteins A and C, fibrinogen, herceptin, leptin, glycosidases, HS-glycoprotein, serum proteins (e.g., α-acid glycoprotein, fetuin, α-fetal protein), β2-glycoprotein, among many others. This list of polypeptides is exemplary, not exclusive. The peptide component of the conjugate can also include fusion and chimeric proteins, including, but not limited to, chimeric proteins that include a moiety derived from an immunoglobulin, such as IgG, or a fragment of an immunoglobin, e.g., FAb (Fc domain). Still further exemplary peptides, which can be modified by the methods of the invention are set forth in Appendix 1. The exemplary peptides provided herein are intended to provide a selection of the peptides with which the present invention can be practiced; as such, they are non-limiting. Those of skill will appreciate that the invention can be practiced using substantially any peptide from any source.

Peptides components of the conjugates of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-aceylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used.

Moreover, in addition to peptides, component of the conjugate that is conjugated with the branched water-soluble polymer of the present invention can be a biological structure other than a peptide (e.g., glycolipids, lipids, sphingoids, ceramides, whole cells, and the like).

Addition of glycosylation sites to a peptide or other structure is conveniently accomplished by altering the amino acid sequence such that it contains one or more glycosylation sites. The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The conjugates of the invention may also include a peptide to which has been added, or from which has been removed, one or more selected glycosyl residues, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N- and O-glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In one embodiment, the invention provides a method for linking two or more peptides through a linking group. The linking group is of any useful structure and may be selected from straight-chain and branched chain structures. Preferably, each terminus of the linker, which is attached to a peptide, includes a modified sugar (i.e., a nascent intact glycosyl linking group).

In an exemplary method of the invention, two peptides are linked together via a linker moiety that includes a branched water-soluble polymer linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Modified Sugars

Modified glycosyl donor species ("modified sugars") are preferably selected from modified sugar nucleotides, activated modified sugars and modified sugars that are simple saccharides that are neither nucleotides nor activated. Any desired carbohydrate structure can be incorporated into a conjugate of the invention. Typically, the structure will be a monosaccharide, but the present invention is not limited to the use of modified monosaccharide sugars; oligosaccharides and polysaccharides are useful as well.

The modifying group is attached to a sugar moiety by enzymatic means, chemical means or a combination thereof, thereby producing a modified sugar. The sugars are substituted at any position that allows for the attachment of the modifying moiety, yet which still allows the sugar to function as a substrate for the enzyme used to ligate the modified sugar to the peptide. In a preferred embodiment, when sialic acid is the sugar, the sialic acid is substituted with the modifying group at either the 9-position on the pyruvyl side chain or at the 5-position on the amine moiety that is normally acetylated in sialic acid.

In certain embodiments of the present invention, a modified sugar nucleotide is utilized to add the modified sugar to the peptide. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the modified sugar nucleotide is selected from an UDP-galactose, UDP-galactosamine, UDP-glucose, UDP-glucosamine, GDP-mannose, GDP-fucose, CMP-sialic acid, or CMP-NeuAc. N-acetylamine derivatives of the sugar nucletides are also of use in the method of the invention.

The invention also provides methods for synthesizing a modified peptide using a modified sugar, e.g., modified-galactose, -fucose, -GalNAc and -sialic acid. When a modified sialic acid is used, either a sialyltransferase or a trans-sialidase (for α2,3-linked sialic acid only) can be used in these methods.

In other embodiments, the modified sugar is an activated sugar. Activated modified sugars, which are useful in the present invention are typically glycosides which have been synthetically altered to include an activated leaving group. As used herein, the term "activated leaving group" refers to those moieties, which are easily displaced in enzyme-regulated nucleophilic substitution reactions. Many activated sugars are known in the art. See, for example, Vocadlo et. al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of activating groups (leaving groups) include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a further exemplary embodiment, the modified sugar is an oligosaccharide having an antennary structure. In a preferred embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the peptide attaches multiple copies of the modifying group to the peptide. The general structure of a typical conjugate of the invention as set forth in the drawing above, encompasses multivalent species resulting from preparing a conjugate of the invention utilizing an antennary structure. Many antennary saccharide structures are known in the art, and the present method can be practiced with them without limitation.

In general, the sugar moiety and the modifying group are linked together through the use of reactive groups, which are typically transformed by the linking process into a new organic functional group or unreactive species. The sugar reactive functional group(s), is located at any position on the sugar moiety.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000)).

In an exemplary embodiment, the peptide that is modified by a method of the invention is a glycopeptide that is produced in prokaryotic cells (e.g., *E. coli*), eukaryotic cells including yeast and mammalian cells (e.g., CHO cells), or in a transgenic animal and thus contains N- and/or O-linked oligosaccharide chains, which are incompletely sialylated. The oligosaccharide chains of the glycopeptide lacking a sialic acid and containing a terminal galactose residue can be glyco-PEG-ylated, glyco-PPG-ylated or otherwise modified with a modified sialic acid.

In Scheme 2, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG or PPG attachment by reacting compound 3 with an activated (m-) PEG or (m-) PPG derivative (e.g., PEG-C(O)NHS, PPG-C(O)NHS), producing 4 or 5, respectively.

Scheme 2

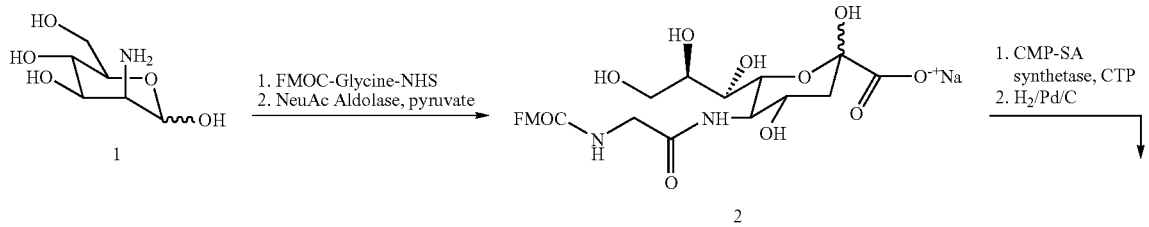

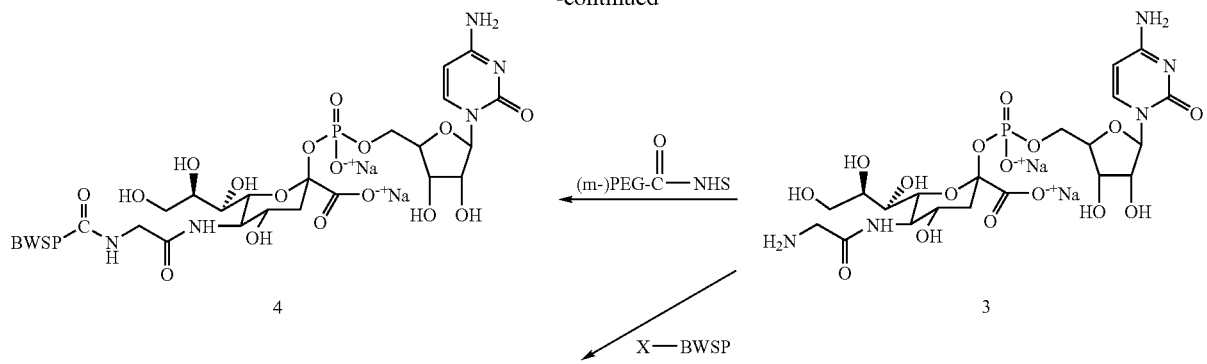

in which X-BWSP is an activated branched water-soluble polymer of the invention, and BWSP is a branched water-soluble polymer.

Table 2 sets forth representative examples of sugar monophosphates that are derivatized with a PEG or PPG moiety. Certain of the compounds of Table 2 are prepared by the method of Scheme 4. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 2

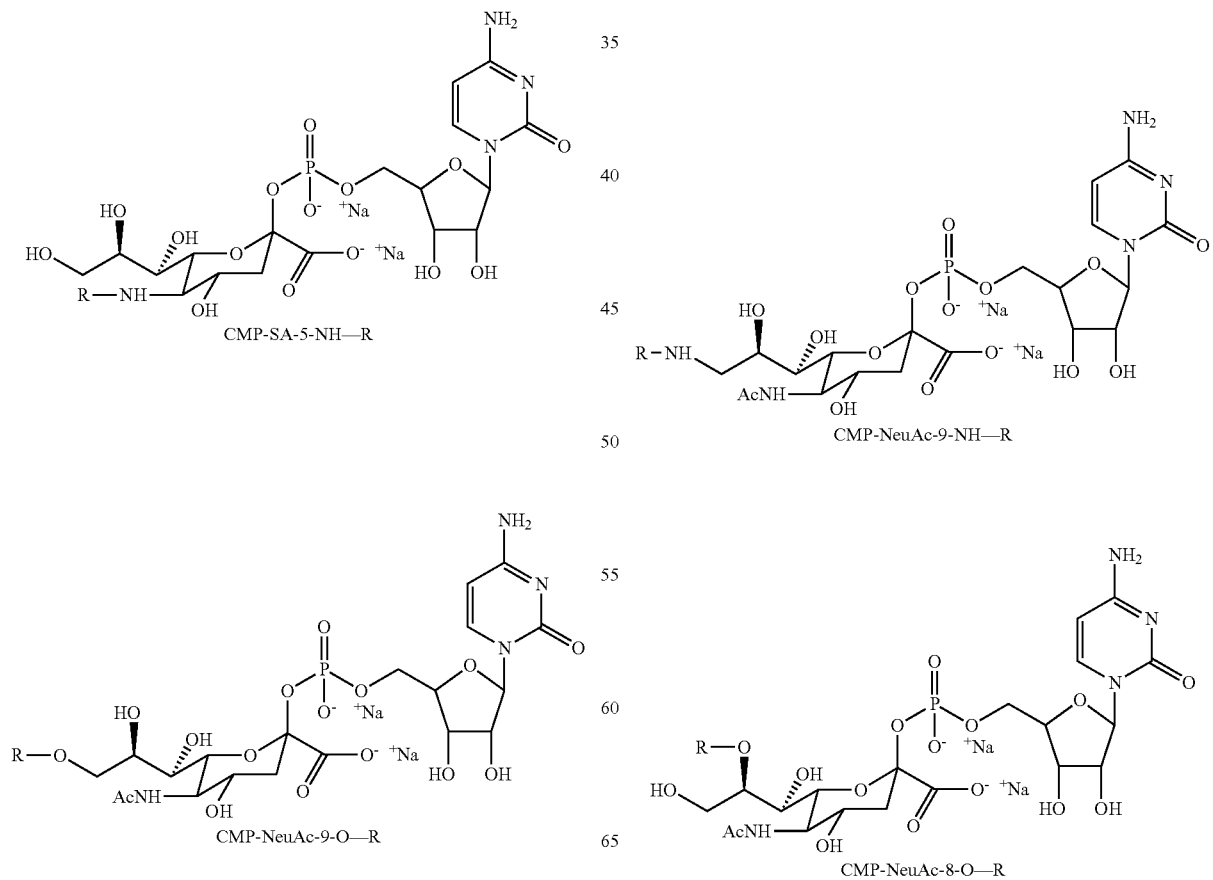

TABLE 2-continued

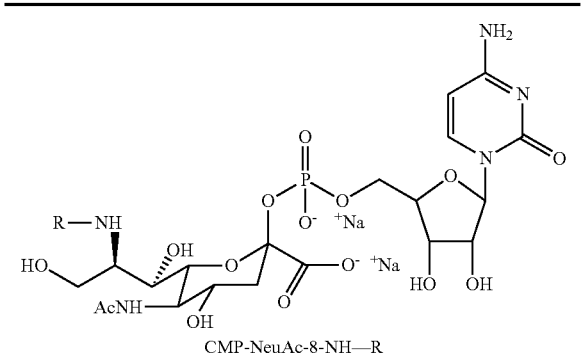

CMP-NeuAc-8-NH—R

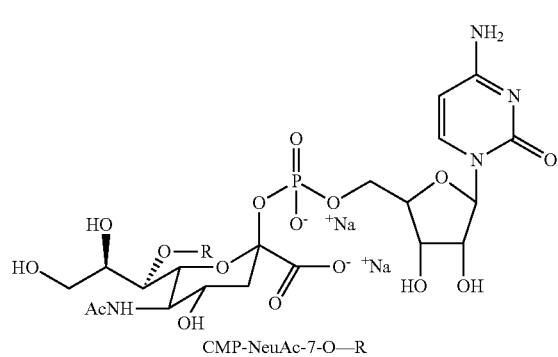

CMP-NeuAc-7-O—R

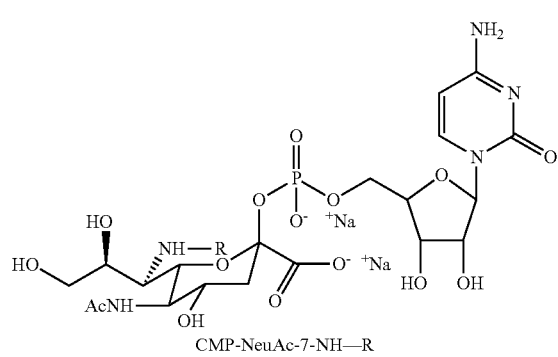

CMP-NeuAc-7-NH—R

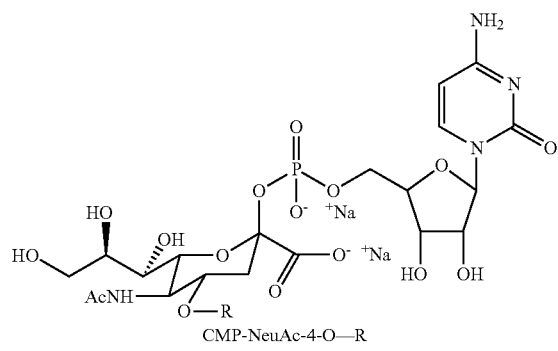

CMP-NeuAc-4-O—R

TABLE 2-continued

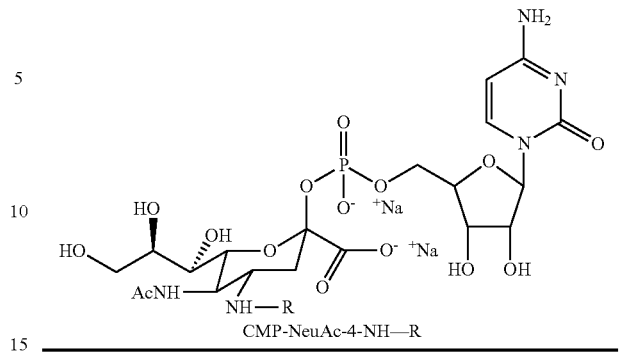

CMP-NeuAc-4-NH—R in which R is a branched water-soluble polymer of the present invention.

The modified sugar phosphates of use in practicing the present invention can be substituted in other positions as well as those set forth above. Presently preferred substitutions of sialic acid are set forth below:

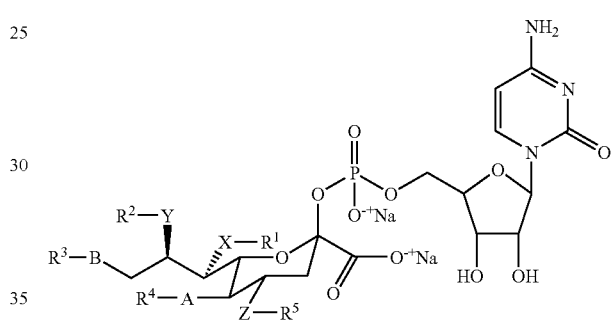

in which X is a linking group, which is preferably selected from —O—, —N(H)—, —S, $CH_2$—, and —N(R)$_2$, in which each R is a member independently selected from $R^1$-$R^5$. The symbols Y, Z, A and B each represent a group that is selected from the group set forth above for the identity of X, X, Y, Z, A and B are each independently selected and, therefore, they can be the same or different. The symbols $R^1$, $R^2$, $R^3$, $R^4$ and $R^5$ represent H, or a branched water-soluble polymer. Alternatively, these symbols represent a linker that is bound to a branched water-soluble polymer.

Cross-Linking Groups

Preparation of the modified sugar for use in the methods of the present invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH((S-(2-thiopyridyl)mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS(N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

i. Preferred Specific Sites in Crosslinking Reagents

1. Amino-Reactive Groups

In one preferred embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

2. Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodimide (Yamada et al., *Biochemistry* 20: 4836-4842, 1981).

ii. Preferred Nonspecific Sites in Crosslinking Reagents

In addition to the use of site-specific reactive moieties, the present invention contemplates the use of non-specific reactive groups to link the sugar to the modifying group.

Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

iii. Homobifunctional Reagents

I. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOES), ethylene glycol-bis(succinimidylsuccinate) (EGS), ethylene glycolbis (sulfosuccinimidylsuccinate) (sulfo-EGS), dithiobis (succinimidyl-propionate (DSP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3, 3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylhydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

iv. HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4-((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et. al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

v. Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

The Methods

The invention also provides a method of preparing an essentially mono-disperse population of poly(ethylene glycol) molecules. The method includes contacting a PEG molecule with a well-defined molecular weight, e.g., PEG200 with at least two equivalents of a bifunctional activated PEG that also has a well-defined molecular weight, e.g., PEG200, thereby producing a mono-disperse sample of a PEG, e.g., PEG600:

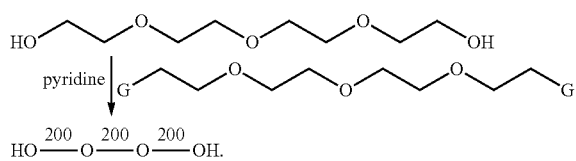

G is a leaving group, such as a sulfonate or tresylate ester. The mono-disperse sample of PEG600 can then be contacted with the bifunctional activated PEG200 to form a mono-disperse PEG100. Alternatively, the mono-disperse PEG600 can be converted to the corresponding bifunctional derivative and reacted with at least two equivalents of a mono-disperse di-hydroxy-PEG600, producing a mono-disperse PEG 1800. The process of the invention is repeated until a mono-disperse PEG of the desired size is obtained. The synthesis can be designed such that the molecular weight differences between the starting material and the product allow for the separation of any unreacted or partially reacted materials by size exclusion chromatography.

Activated PEG Derivatives

The present invention also provides a method of preparing a derivative of poly(ethylene glycol). The method is outlined in Scheme I:

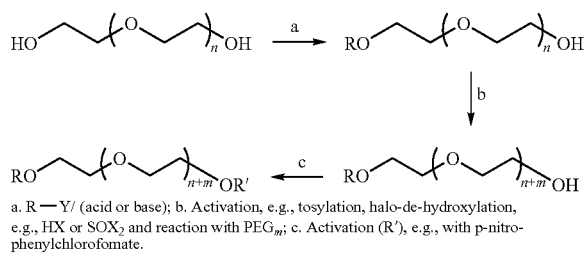

a. R—Y/ (acid or base); b. Activation, e.g., tosylation, halo-de-hydroxylation, e.g., HX or SOX$_2$ and reaction with PEG$_m$; c. Activation (R'), e.g., with p-nitro-phenylchlorofomate.

in which the indexes m and n independently represent integers from 1 to 100,000. R is a member selected from substituted or unsubstituted alkyl, substituted or unsubstituted heteroalkyl, substituted or unsubstituted aryl, alkylamine, protected alkylamine, or an activating group, e.g., triflate, tosylate and the like.

R' is selected from substituted or unsubstituted alkyl, substituted or unsubstituted heteroalkyl, substituted or unsubstituted aryl, substituted or unsubstituted heterocycloalkyl and substituted or unsubstituted heteroaryl. When R does not include a leaving group for activating the CH$_2$—O moiety to which it is attached, R' generally is, or includes, a leaving group.

In an exemplary embodiment, R is lower alkyl, such as methyl. In another exemplary embodiment, R' is substituted alkyl, such a p-nitrophenyl chloroformate.

In step a, the starting glycol is contacted with an activated group (R—Y) that reacts with a hydroxyl moiety of the glycol. Y is generally a leaving group, allowing placement of R on one of the hydroxyl moieties of the PEG molecule. In step b, the free hydroxyl of the resulting adduct is activated by its conversion to a group such as a halide, e.g., chloro or sulfonate ester, e.g., tosylate. The activated PEG species is contacted with another PEG moiety of the same or different degree of polymerization as the starting PEG ("PEG$_m$"). To allow its attachment to another species, the RO-PEG$_{(n+m)}$ is optionally activated at the free hydroxyl moiety.

In general, the R group is attached to the PEG moiety via a species that includes a reactive functional group. Moreover, the two poly(ethylene glycol) fragments are linked together through the use of reactive functional groups, which are typically transformed by the linking process into a new organic functional group or unreactive species. The reactive functional group(s), is located at any position on the of the poly (ethylene glycol) moiety, but is preferably at one of the termini.

Conjugation of Branched Polymer-Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et. al., Pure Appl. Chem. 65: 753 (1993), and U.S. Pat. Nos. 5,352, 670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

The O-linked glycosyl moieties of the conjugates of the invention are generally originate with a GalNAc moiety that is attached to the peptide. Any member of the family of GalNAc transferases can be used to bind a GalNAc moiety to the peptide (Hassan H, Bennett EP, Mandel U, Hollingsworth M A, and Clausen H (2000). Control of Mucin-Type O-Glycosylation: O-Glycan Occupancy is Directed by Substrate Specificities of Polypeptide GalNAc-Transferases. (Eds. Ernst, Hart, and Sinay). Wiley-VCH chapter "Carbohydrates in Chemistry and Biology—a Comprehension Handbook", 273-292). The GalNAc moiety itself can be the intact glycosyl linker. Alternatively, the saccharyl residue is built out using one more enzyme and one or more appropriate glycosyl substrate for the enzyme, the modified sugar being added to the built out glycosyl moiety.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated peptide. The exemplary modified sialic acid is labeled with (m-) PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of branched polymer modified-carbohydrates onto a peptide or glycopeptide. The method utilizes modified sugars containing a branched water-soluble polymer, and is combined with the appropriate glycosyltransferase or glycosynthase. By selecting the glycosyltransferase that will make the desired carbohydrate linkage and utilizing the modified sugar as the donor substrate, the branched water-soluble polymer can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as GalNAc, Galβ1,4GlcNAc, Galβ1,4GalNAc, Galβ1,3GalNAc, lacto-N-tetraose, Galβ1,3GlcNAc, Galβ1,3Ara, Galβ1, 6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In an exemplary embodiment, a carbohydrate residue is "trimmed" prior to the addition of the modified sugar. For example a GalNAc-Gal residue is trimmed back to GalNAc. A modified sugar bearing a water-soluble polymer is conjugated to one or more of the sugar residues exposed by the "trimming." In one example, a glycopeptide is "trimmed" and a water-soluble polymer is added to the resulting O-side chain amino acid or glycopeptide glycan via a saccharyl moiety, e.g., Sia, Gal or GalNAc moiety conjugated to the water-soluble polymer. The modified saccharyl moiety is attached to an acceptor site on the "trimmed" glycopeptide. Alternatively, an unmodified saccharyl moiety, e.g., Gal can be added the terminus of the O-linked glycan.

In another exemplary embodiment, a branched water-soluble polymer is added to a GalNAc residue via a modified sugar having a galactose residue. Alternatively, an unmodified Gal can be added to the terminal GalNAc residue.

In yet a further example, a branched water-soluble polymer is added onto a Gal residue using a modified sialic acid.

The exemplary embodiments discussed above provide an illustration of the power of the methods set forth herein. Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, the branched water-soluble polymer is added to a terminal Gal residue using a polymer modified sialic acid. An appropriate sialyltransferase is used to add a modified sialic acid. The approach is summarized in Scheme 3.

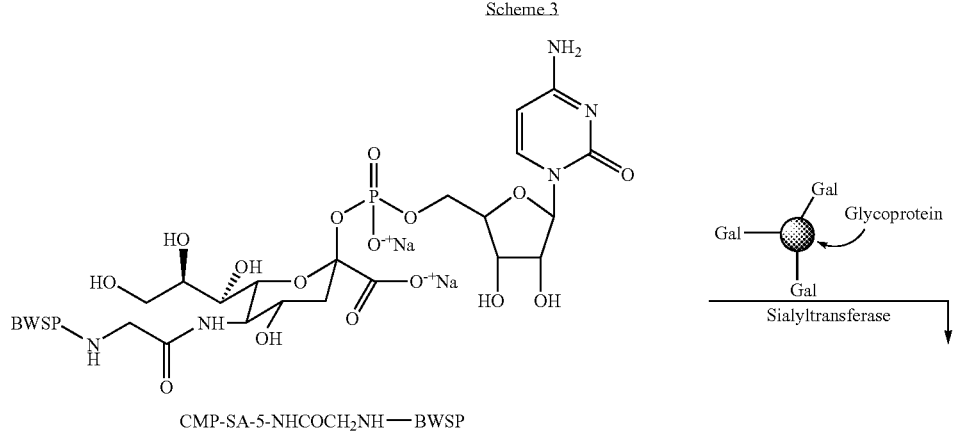

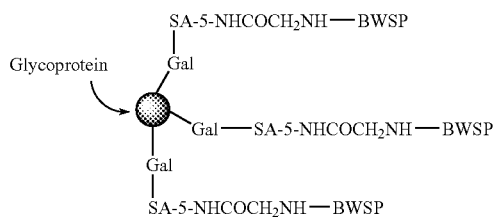

In yet a further approach, summarized in Scheme 4, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

Scheme 4

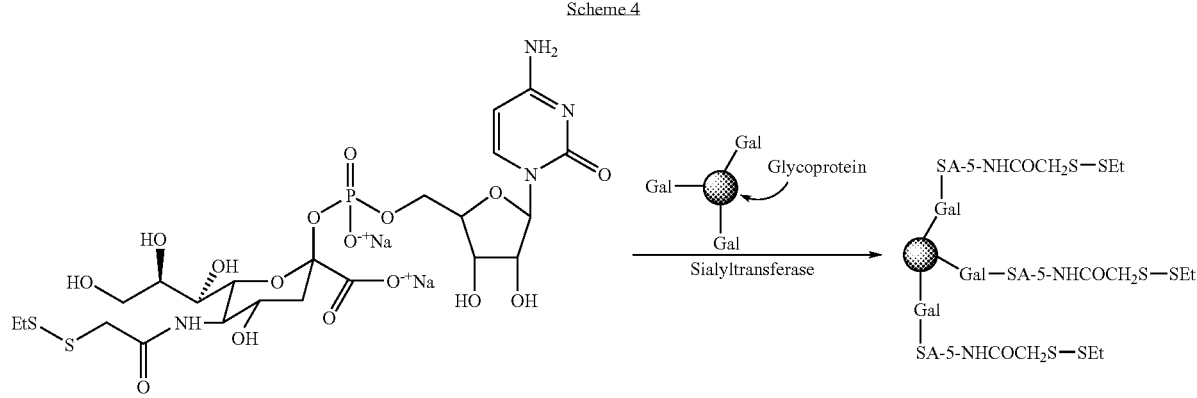

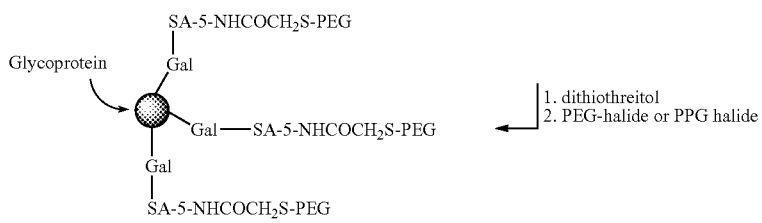

Any modified sugar can be used with its appropriate glycosyltransferase, depending on the terminal sugars of the oligosaccharide side chains of the glycopeptide (Table 3). As discussed above, the terminal sugar of the glycopeptide required for introduction of the branched water-soluble polymer structure can be introduced naturally during expression or it can be produced post expression using the appropriate glycosidase(s), glycosyltransferase(s) or mix of glycosidase(s) and glycosyltransferase(s).

TABLE 3

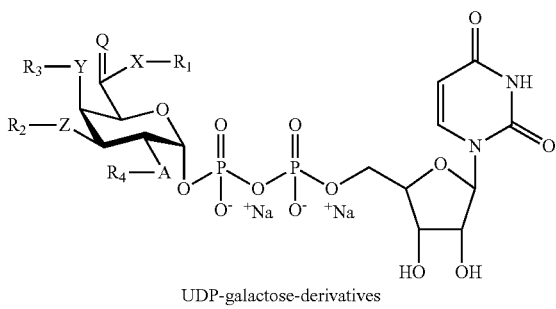

UDP-galactose-derivatives

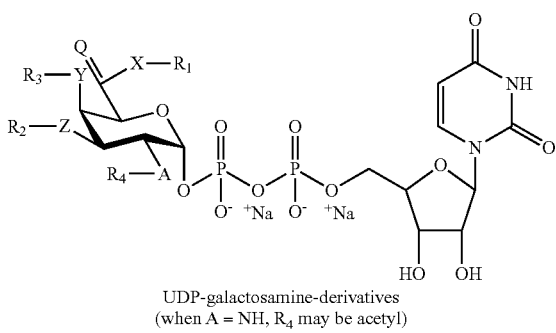

UDP-galactosamine-derivatives
(when A = NH, $R_4$ may be acetyl)

TABLE 3-continued

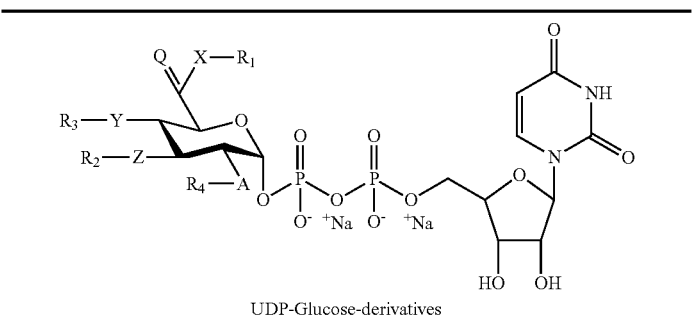
UDP-Glucose-derivatives

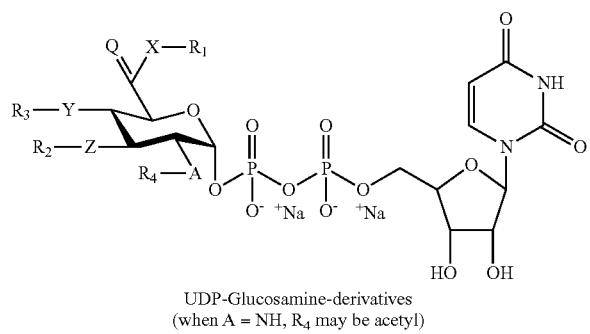
UDP-Glucosamine-derivatives
(when A = NH, R$_4$ may be acetyl)

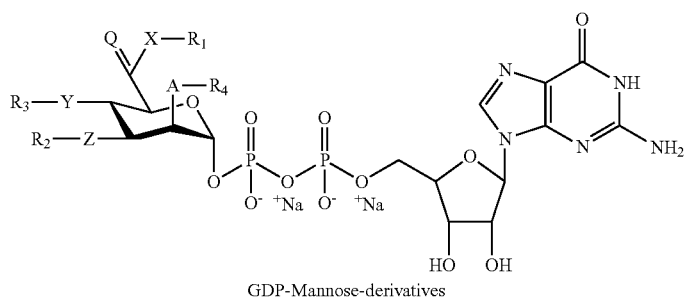
GDP-Mannose-derivatives

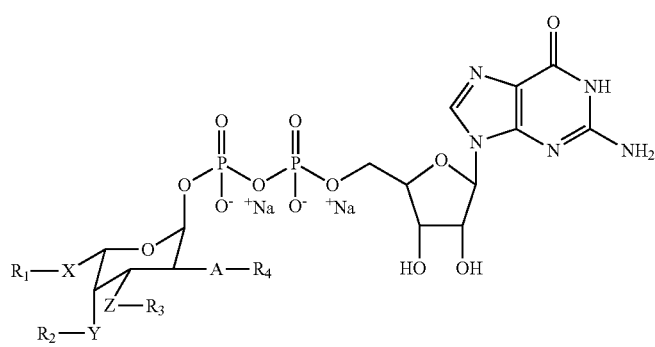
GDP-fucose-derivatives

X = O, NH, S, CH$_2$, N—(R$_{1-5}$)$_2$.
Y = X; Z = X; A = X; B = X.
Q = H$_2$, O, S, NH, N—R.
R, R$_{1-4}$ = H, Linker-M, M.
M = branched water-soluble peptide In an alternative embodiment, the modified sugar is added directly to the peptide backbone using a glycosyltransferase known to transfer sugar residues to the O-linked glycosylation site on the peptide backbone. This exemplary embodiment is set forth in Scheme 5. Exemplary glycosyltransferases useful in practicing the present invention include, but are not limited to, GalNAc transferases (GalNAc T1-20), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

Scheme 5

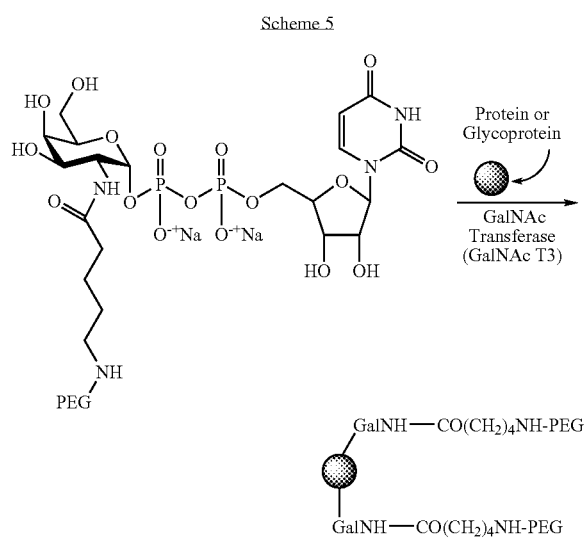

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

In another exemplary embodiment, the glycopeptide is conjugated to a targeting agent, e.g., transferrin (to deliver the peptide across the blood-brain barrier, and to endosomes), carnitine (to deliver the peptide to muscle cells; see, for example, LeBorgne et al., *Biochem. Pharmacol.* 59: 1357-63 (2000), and phosphonates, e.g., bisphosphonate (to target the peptide to bone and other calciferous tissues; see, for example, Modern Drug Discovery, August 2002, page 10). Other agents useful for targeting are apparent to those of skill in the art. For example, glucose, glutamine and IGF are also useful to target muscle.

The targeting moiety and therapeutic peptide are conjugated by any method discussed herein or otherwise known in the art. Those of skill will appreciate that peptides in addition to those set forth above can also be derivatized as set forth herein. Exemplary peptides are set forth in the Appendix attached to copending, commonly owned U.S. Provisional Patent Application No. 60/328,523 filed Oct. 10, 2001.

In an exemplary embodiment, the targeting agent and the therapeutic peptide are coupled via a linker moiety. In this embodiment, at least one of the therapeutic peptide or the targeting agent is coupled to the linker moiety via an intact glycosyl linking group according to a method of the invention. In an exemplary embodiment, the linker moiety includes a poly(ether) such as poly(ethylene glycol). In another exemplary embodiment, the linker moiety includes at least one bond that is degraded in vivo, releasing the therapeutic peptide from the targeting agent, following delivery of the conjugate to the targeted tissue or region of the body.

In yet another exemplary embodiment, the in vivo distribution of the therapeutic moiety is altered via altering a glycoform on the therapeutic moiety without conjugating the therapeutic peptide to a targeting moiety. For example, the therapeutic peptide can be shunted away from uptake by the reticuloendothelial system by capping a terminal galactose moiety of a glycosyl group with sialic acid (or a derivative thereof).

i. Enzymes

1. Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferases, fucosyltransferase, sialyltransferase, mannosyltransferase, xylosyltransferases, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglycosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferase may be synthesized in host cells transformed with vectors containing DNA encoding the glycosyltransferases enzyme. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the invention utilizes a prokaryotic enzyme. Such glycosyltransferases include enzymes involved in synthesis of lipooligosaccharides (LOS), which are produced by many gram negative bacteria (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. 556361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK) (EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum,* and the rhl operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the P$^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the P$^k$ blood group antigen structure (Gotshlich (1994), supra.). In *N. meningitidis*, a separate immunotype L1 also expresses the P$^k$ blood group antigen and has been shown to carry an lgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

a) Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→→3,4)fucosyltransferase (FTIII E.C. No. 2.4.1.65), which was first characterized from human milk (see, Palcic, et al., *Carbohydrate Res.* 190:1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβfucosyltransferase, has also been characterized. A recombinant form of the Galβ(1→3,4) GlcNAcβ-α (1→3,4)fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, α-1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

b) Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et. al., *Immunogenetics* 41: 101-105 (1995)). Another suitable α-1,3 galactosyltransferase is that which is involved in synthesis of the blood group B antigen (EC 2.4.1.37, Yamamoto et al., *J. Biol. Chem.* 265: 1146-1151 (1990) (human)). Yet a further exemplary galactosyltransferase is core Gal-T1.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. I Biochem.* 183: 211-217 (1989)), human (Masri et al., *Biochem. Biophys. Res. Commun.* 157: 657-663 (1988)), murine (Nakazawa et al., *J. Biochem.* 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

c) Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α-2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 4).

TABLE 4

Sialyltransferases which use the Galβ1,4G1cNAc sequence as an acceptor substrate

| Sialyltransferase | Source | Sequence(s) formed | Ref. |
|---|---|---|---|
| ST6Gal I | Mammalian | NeuAcI2,6Galβ1,4G1CNAc- | 1 |
| ST3Gal III | Mammalian | NeuAcI2,3Galβ1,4G1CNAc- NeuAcI2,3Galβ1,3G1CNAc- | 1 |
| ST3Gal IV | Mammalian | NeuAcI2,3Galβ1,4G1CNAc- NeuAcI2,3Galβ1,3G1CNAc- | 1 |
| ST6Gal II | Mammalian | NeuAcI2,6Galβ1,4G1CNA | |
| ST6Gal II | photobacterium | NeuAcI2,6Galβ1,4G1CNAc- | 2 |
| ST3Gal V | *N. meningitides N. gonorrhoeae* | NeuAcI2,3Galβ1,4G1CNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.*

268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from *Campylobacter jejuni*, including the α(2,3). See, e,g, WO99/49051.

Sialyltransferases other those listed in Table 5, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$\alpha_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

d) GalNAc transferases

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3) N-acetylgalactosaminyltransferases, β(1,4) N-acetylgalactosaminyltransferases (Nagata et al., *J. Biol. Chem.* 267: 12082-12089 (1992) and Smith et al., *J. Biol. Chem.* 269: 15162 (1994)) and polypeptide N-acetylgalactosaminyltransferase (Homa et al., *J. Biol. Chem.* 268: 12609 (1993)).

Production of proteins such as the enzyme GalNAc $T_{I-XX}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

2. Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); U18918), and glycosaminoglycan N-acetylglucosamine N-deacetylase/N-sulphotransferase 2 (murine cDNA described in Orellana et al., *J. Biol. Chem.*

269: 2270-2276 (1994) and Eriksson et al., *J. Biol. Chem.* 269: 10438-10443 (1994); mouse cDNA described in GenBank Accession No. UO2304).

3. Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose: β.-D-galactosyl-1,4-N-acetyl-D-glucosaminide α-1,3-galactosyltransferase was transfected into COS-1 cells. The transfected cells were then cultured and assayed for a 1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

4. Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

5. Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Purification of Peptide Conjugates

The products produced by the above processes can be used without purification. However, it is usually preferred to recover the product. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the modified glycoprotein is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, SP-Sepharose, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps, e.g., SP Sepharose. Additionally, the modified glycoprotein may be purified by affinity chromatography. HPLC may also be employed for one or more purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which sproduce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

The modified glycopeptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

In addition to the conjugates discussed above, the present invention provides methods for preparing these and other conjugates. Moreover, the invention provides methods of preventing, curing or ameliorating a disease state by administering a conjugate of the invention to a subject at risk of developing the disease or a subject that has the disease.

Pharmaceutical Compositions

Therapeutic moieties that are conjugated to branched water-soluble polymers of the present invention have a broad range of pharmaceutical applications. For example, modified erythropoietin (EPO) may be used for treating general anemia, aplastic anemia, chemo-induced injury (such as injury to bone marrow), chronic renal failure, nephritis, and thalassemia. Modified EPO may be further used for treating neurological disorders such as brain/spine injury, multiple sclerosis, and Alzheimer's disease.

A second example is interferon-α (IFN-α), which may be used for treating AIDS and hepatitis B or C, viral infections caused by a variety of viruses such as human papilloma virus (HBV), coronavirus, human immunodeficiency virus (HIV), herpes simplex virus (HSV), and varicella-zoster virus (VZV), cancers such as hairy cell leukemia, AIDS-related Kaposi's sarcoma, malignant melanoma, follicular non-Hodgkins lymphoma, Philladephia chromosome (Ph)-positive, chronic phase myelogenous leukemia (CML), renal cancer, myeloma, chronic myelogenous leukemia, cancers of the head and neck, bone cancers, as well as cervical dysplasia and disorders of the central nervous system (CNS) such as multiple sclerosis. In addition, IFN-α modified according to the methods of the present invention is useful for treating an assortment of other diseases and conditions such as Sjogren's syndrome (an autoimmune disease), Behcet's disease (an autoimmune inflammatory disease), fibromyalgia (a musculoskeletal pain/fatigue disorder), aphthous ulcer (canker sores), chronic fatigue syndrome, and pulmonary fibrosis.

Another example is interferon-β, which is useful for treating CNS disorders such as multiple sclerosis (either relapsing/remitting or chronic progressive), AIDS and hepatitis B or C, viral infections caused by a variety of viruses such as human papilloma virus (HBV), human immunodeficiency virus (HIV), herpes simplex virus (HSV), and varicella-zoster virus (VZV), otological infections, musculoskeletal infections, as well as cancers including breast cancer, brain cancer, colorectal cancer, non-small cell lung cancer, head and neck cancer, basal cell cancer, cervical dysplasia, melanoma, skin cancer, and liver cancer. IFN-β modified according to the methods of the present invention is also used in treating other diseases and conditions such as transplant rejection (e.g., bone marrow transplant), Huntington's chorea, colitis, brain inflammation, pulmonary fibrosis, macular degeneration, hepatic cirrhosis, and keratoconjunctivitis.

Granulocyte colony stimulating factor (G-CSF) is a further example. G-CSF modified according to the methods of the present invention may be used as an adjunct in chemotherapy for treating cancers, and to prevent or alleviate conditions or complications associated with certain medical procedures, e.g., chemo-induced bone marrow injury; leucopenia (general); chemo-induced febrile neutropenia; neutropenia associated with bone marrow transplants; and severe, chronic neutropenia. Modified G-CSF may also be used for transplantation; peripheral blood cell mobilization; mobilization of peripheral blood progenitor cells for collection in patients who will receive myeloablative or myelosuppressive chemotherapy; and reduction in duration of neutropenia, fever, antibiotic use, hospitalization following induction/consolidation treatment for acute myeloid leukemia (AML). Other conditions or disorders may be treated with modified G-CSF include asthma and allergic rhinitis.

As one additional example, human growth hormone (hGH) modified according to the methods of the present invention may be used to treat growth-related conditions such as dwarfism, short-stature in children and adults, cachexia/muscle wasting, general muscular atrophy, and sex chromosome abnormality (e.g., Turner's Syndrome). Other conditions may be treated using modified hGH include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomia. Moreover, modified hGH may also be used to promote various processes, e.g., general tissue regeneration, bone regeneration, and wound healing, or as a vaccine adjunct.

Thus, in another aspect, the invention provides a pharmaceutical composition. The pharmaceutical composition includes a pharmaceutically acceptable diluent and a covalent conjugate between a non-naturally-occurring, water-soluble polymer, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable matrises, such as microspheres (e.g., polylactate polyglycolate), may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered subcutaneously or parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235, 871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

The following examples are provided to illustrate the compounds, and methods and of the present invention, but not to limit the claimed invention.

EXAMPLES

The following nomenclature is employed in Examples 1-3. The primary PEG subunit consists of four ethylene glycol units. This molecule has a molecular weight of 194, which has been rounded to 200 in the figures. The following nomenclature is used to represent the primary PEG subunit:

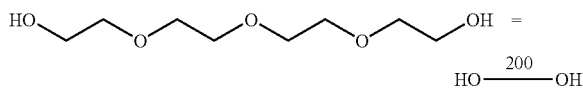

Combinations of primary PEG subunits can be alternatively written with the rounded molecular weight shown between the functionalized ends as shown below.

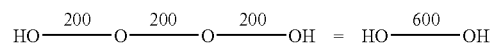

The following nomenclature is used to represent a mono-functionalized methoxy-PEG subunit:

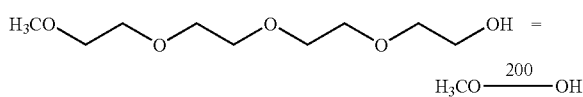

Example 1

The Preparation of Mono-Dispersed PEGs and their Activated Forms

Mono-dispersed or single molecular weight PEGs are prepared as shown below. By adjusting the size of the fragments generated, any size PEG is prepared. The diols are then mono-terminated via alkylation and activated for conjugation to a biological moiety such as a protein, sugar, lipid, or nucleotide.

Leaving groups can be attached to the primary PEG subunit in order to create an activated primary PEG as shown below. In this reaction, Q can be any leaving group that is compatible with the chemistry of this invention. Exemplary leaving groups include halides, tresylates, tosylates and mesylates.

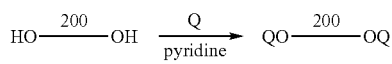

After creating the activated primary PEG, the compound is reacted with primary PEG subunits as shown below. The product is a first generation PEG extension.

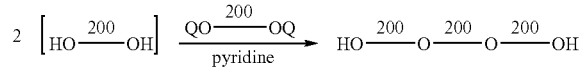

The second generation PEG extension is created in a similar manner as the first generation.

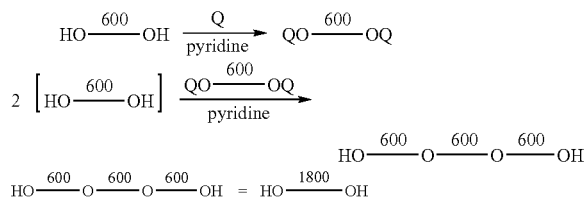

The third generation PEG extension is created as shown below.

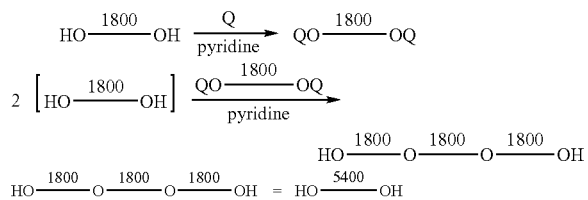

The fourth generation PEG extension is created as shown below.

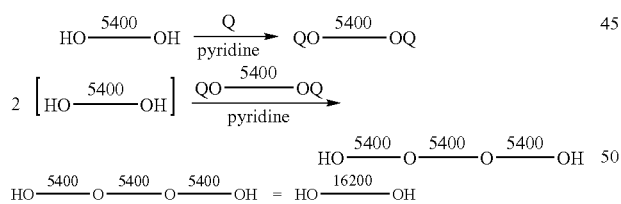

The PEG extension process is terminated by reacting a mono-functionalized moiety with one of the bi-functional compounds. In this reaction, the mono-functionalized moiety is any group that is compatible with the chemistry of this invention. Exemplary terminating groups include alkoxy-PEG and alkyl.

In the following exemplary embodiment, a leaving group is added to a methoxy-PEG subunit. This molecule is then reacted with a fourth generation PEG extension.

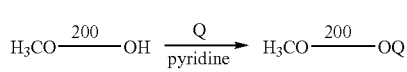

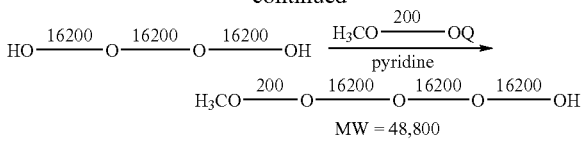

In another exemplary embodiment, a methyl subunit is added to a fourth generation PEG extension.

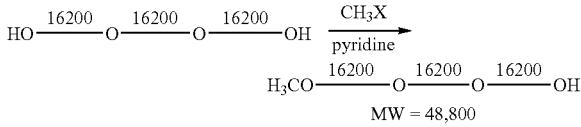

After terminating one end, the other end of the PEG extension is activated for bioconjugation as shown below. In this reaction, X is any leaving group that enables the formation of an ester. The symbol X is independently selected from imidazolyl, HOBt, HOAt, NHS, and p-nitrophenyl ester.

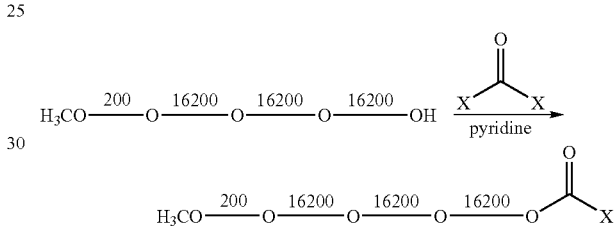

Finally, the PEG extension molecule is conjugated to a biological moiety as shown below.

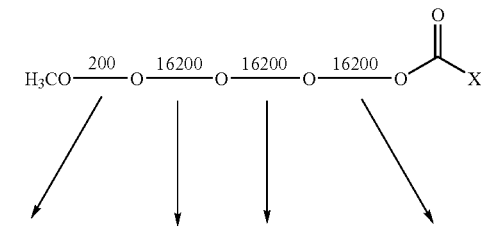

Example 2

There is no requirement that the activated mono-dispersed PEG must have the same number of PEG subunits as the extension molecules to which it reacts. In an exemplary embodiment, the activated mono-dispersed PEG has a larger number of PEG subunits than the extension molecule to which it reacts. In another exemplary embodiment shown below, the activated mono-dispersed PEG has a smaller number of PEG subunits than the extension molecule to which it reacts.

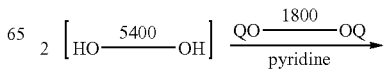

-continued

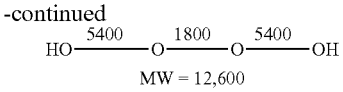
MW = 12,600

The termination process for these molecules is similar to the process described in Example 1.

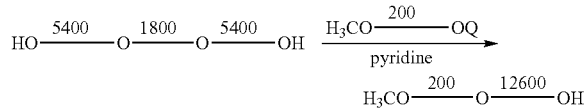

Example 3

An excess of the activated PEG subunit can be added to create the mono-dispersed PEG shown below:

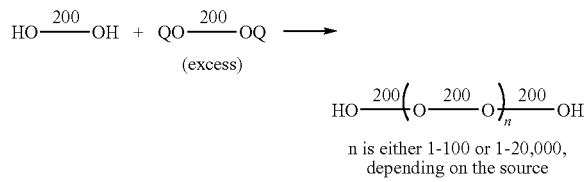

n is either 1-100 or 1-20,000, depending on the source

By varying the ratio of reactants, the based used, temperature, solvent, and concentration, one can adjust the reaction to give the predominant size (n) desired.

This approach provides a simple, fast, efficient way to prepare mono-dispersed PEGs of any size. Purification is simplified by this approach because of the differences in size (and therefore physicochemical characteristics) of the mono-dispersed PEGs. This allows the use of simple, standard purification techniques such as silica gel, reverse phase cellulose, membrane filtration (nanofiltration and ultrafiltration). The purified PEG diols are then derivatized into any functional form that is desired.

Example 4

The Production of Alkoxy PEGs

The general approach shown below is used to prepare alkoxy-PEGs or other mono-functionalized PEGs.

In a first embodiment, an activated biofunctionalized PEG molecule is created as shown below:

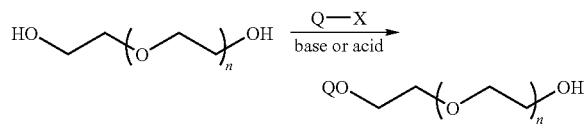

wherein the symbol n represents a number between 1 and 100,000. The symbol Q represents any leaving group that is compatible with the chemistry of this invention. Exemplary leaving groups include halides, tresylates, tosylates and mesylates. The symbol X represents any counter ion that is compatible with the leaving group.

This activated bifunctionalized PEG molecule is used to extend the length of a PEG molecule as shown below:

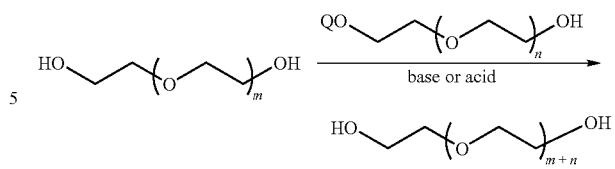

wherein the symbol m represents a number between 1 and 100,000.

In a second embodiment, a mono-functionalized PEG is extended and then activated for use in conjugation with a biological moiety as shown below.

In a first step, a mono-functionalized PEG is tosylated.

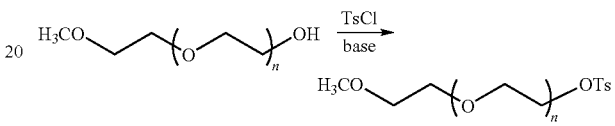

wherein the symbol n represents a number between 1 and 100,000.

In a second step, the mono-functionalized PEG is extended

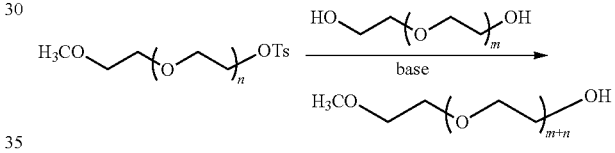

wherein the symbol m represents a number between 1 and 100,000.

In a final step, the extended mono-functionalized PEG compound is activated for conjugation to a biological moiety as shown below.

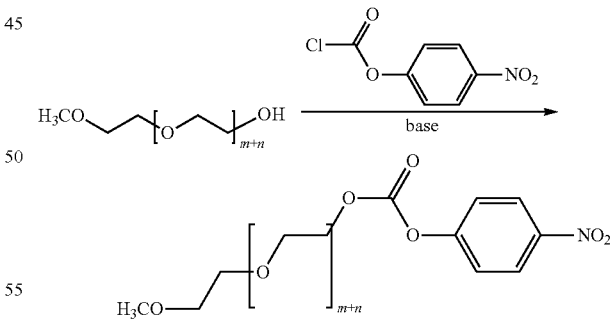

Example 5

Additional Compositions and Methods for the Preparation of Bi-Antennary Polymers Additional bi-antennary structures of the invention have the following general formula:

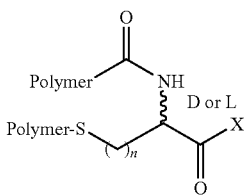

wherein the symbol X represents OH, H, Q (an activating group), and a biological moiety, such as a protein, sugar, lipid, or nucleotide. The symbol n represents a number between 1 and 10. The term "polymer" can be PEG, mPEG (methoxy polyethylene glycol), PPG (polypropylene glycol), mPPG, polyglutamate, polyaspartate, polylactate, and polysialic acid.

In an exemplary embodiment, the bi-antennary structure has the following formula:

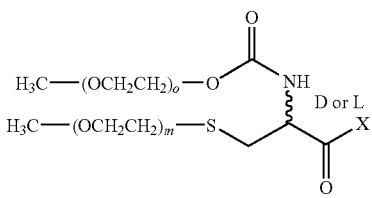

wherein the symbols m and o independently represent numbers between 1 and 10,000. The symbol X represents OH, H, Q (an activating group), and a biological moiety, such as a protein, sugar, lipid, or nucleotide.

In another exemplary embodiment, the bi-antennary structure has the following formula:

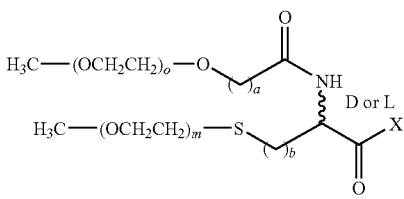

wherein the symbols a and b independently represent numbers between 1 and 24. The symbols m and o independently represent numbers between 1 and 10,000. The symbol X represents OH, H, Q (an activating group), and a biological moiety, such as a protein, sugar, lipid, or nucleotide.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

What is claimed is:

1. A branched water-soluble polymer having the formula:

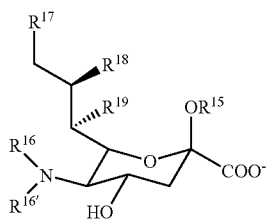

in which
$R^{16}$, $R^{16'}$, $R^{17}$, $R^{18}$ and $R^{19}$ are members independently selected from H, OH, $NH_2$, NHAc and:

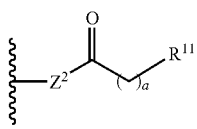

(I)

wherein
$Z^2$ is a member selected from O, S, $CH_2$ and S
$R^{11}$ is a water-soluble polymer, and
the index "a" represents an integer from 0 to 20,
with the proviso that at least two of $R^{16}$, $R^{16'}$, $R^{17}$, $R^{18}$ and $R^{19}$ have a structure according to Formula I; and
$R^{15}$ is a member selected from H, a nucleotide sugar, and a bond to a carrier molecule, wherein the carrier molecule is a member selected from a peptide, glycopeptide, lipid, glycolipid, protein, glycoprotein, saccharide, hormone, receptor, antigen, transition state analog, cofactor, drug, dye, nutrient, growth factor, solid support, virus, and microorganism.

2. The branched water-soluble polymer according to claim 1, wherein said water-soluble polymer comprises poly(ethylene glycol).

3. The branched water-soluble polymer according to claim 1, wherein said carrier molecule is a peptide, glycopeptide, lipid, or glycolipid.

4. The branched water-soluble polymer according to claim 1, wherein $R^{15}$ is a nucleotide sugar.

5. The branched water-soluble polymer according to claim 4, wherein the nucleotide sugar is cytidine monophosphate (CMP).

6. The branched water-soluble polymer according to claim 1, wherein said carrier molecule is a protein, glycoprotein, saccharide, hormone, receptor, antigen, transition state analog, cofactor, drug, dye, nutrient, growth factor, solid support, virus, or microorganism.

7. The branched water-soluble polymer according to claim 2, wherein said poly(ethylene glycol) has a molecular weight selected from 5 kD, 10 kD, 20 kD, and 30 kD.

8. The branched water-soluble polymer according to claim 7, wherein said poly(ethylene glycol) has a molecular weight of 20 kD.

9. The branched water-soluble polymer according to claim 3, wherein said water-soluble polymer comprises poly(ethylene glycol).

10. The branched water-soluble polymer according to claim 9, wherein said poly(ethylene glycol) has a molecular weight selected from 5 kD, 10 kD, 20 kD, and 30 kD.

11. The branched water-soluble polymer according to claim 10, wherein said poly(ethylene glycol) has a molecular weight of 20 kD.

12. A pharmaceutical formulation comprising the branched water-soluble polymer according to claim 1 and a pharmaceutically acceptable carrier.

13. A pharmaceutical formulation comprising the branched water-soluble polymer according to claim 2 and a pharmaceutically acceptable carrier.

14. A pharmaceutical formulation comprising the branched water-soluble polymer according to claim 3 and a pharmaceutically acceptable carrier.

15. A pharmaceutical formulation comprising the branched water-soluble polymer according to claim 7 and a pharmaceutically acceptable carrier.

16. A pharmaceutical formulation comprising the branched water-soluble polymer according to claim 8 and a pharmaceutically acceptable carrier.

17. A pharmaceutical formulation comprising the branched water-soluble polymer according to claim 9 and a pharmaceutically acceptable carrier.

18. A pharmaceutical formulation comprising the branched water-soluble polymer according to claim 10 and a pharmaceutically acceptable carrier.

19. A pharmaceutical formulation comprising the branched water-soluble polymer according to claim 11 and a pharmaceutically acceptable carrier.

* * * * *